United States Patent [19]

Debono et al.

[11] Patent Number: 4,820,695
[45] Date of Patent: Apr. 11, 1989

[54] C-20-DIHYDRO-DEOXY-(CYCLIC AMINO)-DERIVATIVES OF MACROLIDE ANTIBIOTICS

[75] Inventors: Manuel Debono; Herbert A. Kirst, both of Indianapolis, Ind.

[73] Assignee: Eli Lilly and Company, Indianapolis, Ind.

[21] Appl. No.: 54,966

[22] Filed: May 28, 1987

Related U.S. Application Data

[63] Continuation of Ser. No. 645,936, Aug. 30, 1984, abandoned, which is a continuation-in-part of Ser. No. 517,136, Jul. 25, 1983, abandoned, which is a continuation-in-part of Ser. No. 417,247, Sep. 13, 1982, abandoned.

[51] Int. Cl.$^4$ .................... A61K 31/71; C07H 17/08
[52] U.S. Cl. ........................................ 514/30; 536/7.1
[58] Field of Search ......................... 514/30; 536/7.1

[56] References Cited

U.S. PATENT DOCUMENTS

| | | | |
|---|---|---|---|
| 3,178,341 | 4/1965 | Hamill et al. | 435/896 X |
| 3,326,759 | 6/1967 | Hamill et al. | 435/896 X |
| 4,196,280 | 4/1980 | Umezawa et al. | 536/17 R |
| 4,268,665 | 5/1981 | Sakakibara et al. | 546/7.1 |
| 4,279,896 | 7/1981 | Ganguly et al. | 424/180 |
| 4,299,953 | 11/1981 | Hamill et al. | 536/7.1 |
| 4,321,361 | 3/1982 | Baltz et al. | 536/7.1 |
| 4,321,362 | 3/1982 | Baltz et al. | 536/7.1 |
| 4,345,069 | 8/1982 | Sakakibara et al. | 536/7.1 |
| 4,349,665 | 9/1982 | Lee et al. | 536/7.1 |
| 4,357,325 | 11/1982 | Ose et al. | 536/7.1 |
| 4,385,116 | 5/1983 | Baltz et al. | 435/76 |
| 4,435,388 | 3/1984 | Ganguly et al. | 424/180 |
| 4,436,729 | 3/1984 | Ganguly et al. | 424/180 |
| 4,440,759 | 4/1984 | Omura et al. | 424/180 |
| 4,443,436 | 4/1984 | Kirst et al. | 424/180 |
| 4,468,511 | 8/1984 | Kirst et al. | 536/7.1 |

FOREIGN PATENT DOCUMENTS

| | | | |
|---|---|---|---|
| 0021182 | 2/1978 | Japan | 536/7.1 |
| 0130686 | 11/1978 | Japan | 536/7.1 |
| 0132584 | 11/1978 | Japan | 536/7.1 |

OTHER PUBLICATIONS

H. Matsubara et al., "Chemical Transformation of Tylosin, a 16-Membered Macrolide, and Its Structure-Activity Relationship", *Chem. Pharm. Bull.* 30 (1), 97-110, (1982).

S. Omura et al., "Novel Dimeric Derivatives of Leucomycins and Tylosin, Sixteen-Membered Macrolides", *J. Med. Chem.* 25, 271-275, (1982).

Derwent Abstract No. 71396Y of Japanese Unexamined Patent 2100-485 (Takeda), Aug. 23, 1977.

A. Tanaka et al., "Syntheses of 4'-Deoxy-Demycarosyl Tylosin and Its Analogues", *J. Antibiotics* 34 (10), 1381-1384, (1981).

S. Satoi et al., "Mycinamicins, New Macrolide Antibiotic, I: Taxonomy, Production, Isolation, Characterization and Properties", *J. Antibiotics* 33 (4), 364-377, (1980).

A. Tanaka et al., "Synthesis of 23-Dialkylamino Derivatives of Mycaminosyl Tylonolide and 4'-Deoxymycaminosyl Tylonolide Effective Against Gram-negative Bacteria", *J. Antibiotics* 35 (1), 113-116, (1982).

H. Matsubara et al., "Chemical Modification of Tylosin: Synthesis of Amino Derivatives at C-20 Position of Tylosin and Demycarosyltylosin", *J. Antibiotics* 36, 1713-1721, (1983).

Derwent Abstract No. 84-110819/18 of Japanese Unexamined Patent J5 9051-299A (Zh Biseibutsu Kagaku Ken), Mar. 24, 1984.

*Primary Examiner*—Johnnie R. Brown
*Assistant Examiner*—Elli Peselev
*Attorney, Agent, or Firm*—Nancy J. Harrison; Leroy Whitaker

[57] ABSTRACT

C-20-Dihydro-deoxy-(cyclic amino)-derivatives of the macrolide antibiotics tylosin, desmycosin, macrocin, lactenocin, 2'''-O-demethylmacrocin and 2''-O-demethyllactenocin, which inhibit pathogenic bacteria, especially gram-positive bacteria, Pasteurella species, and Mycoplasma species, and pharmaceutical compositions thereof, are provided.

63 Claims, No Drawings

C-20-DIHYDRO-DEOXY-(CYCLIC AMINO)-DERIVATIVES OF MACROLIDE ANTIBIOTICS

CROSS-REFERENCE TO RELATED APPLICATION

This application is a continuation of application Ser. No. 645,936, filed Aug. 30, 1984, now abandoned, which is a continuation-in-part of application Ser. No. 517,136, filed July 25, 1983, now abandoned, which in turn is a continuation-in-part of application Ser. No. 417,247, filed Sept. 13, 1982, now abandoned.

SUMMARY OF THE INVENTION

This invention relates to C-20-modified macrolide derivatives having formulas 1 and 2:

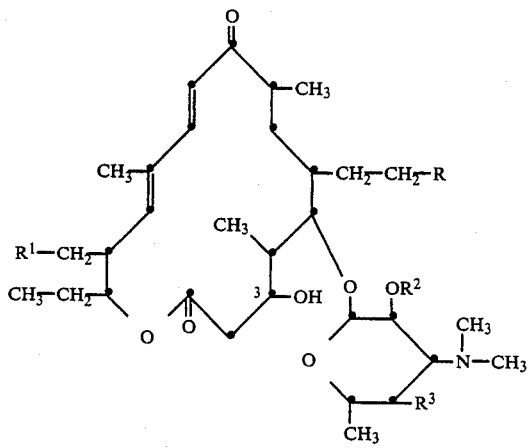

wherein

R is a saturated or unsaturated secondary amino group of the formula

in which the nitrogen atom is part of an otherwise carbocyclic ring system selected from a monocyclic ring containing from 5 to 16 ring atoms or a bicyclic or tricyclic ring system containing from 8 to 20 ring atoms wherein one or more of the carbon atoms may be substituted by $C_1$-$C_4$ alkyl, $C_2$-$C_4$ alkenyl, $C_2$-$C_4$ alkynyl, $C_1$-$C_4$ alkoxy, $C_1$-$C_4$ alkoxycarbonyl, hydroxyl, $C_1$-$C_4$ alkanoyloxy, halo, halo-$C_1$-$C_4$ alkyl, $-N(C_1$-$C_4$ alkyl$)_2$, $-N(CH_2)_m$,

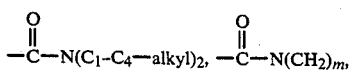

cyano, ethylenedioxy, benzyl, phenyl, or phenyl substituted by from 1 to 3 substituents selected from nitro, halo, $C_1$-$C_4$-alkyl, $C_1$-$C_4$ alkoxy, hydroxy, amino, or mono- or di-($C_1$-$C_4$ alkyl)amino;
m is an integer from 4 through 7;
$R^1$ is HO— [structures shown] —O—; HO— [structures] —O—; or HO— [structure] —O—;

$R^2$ is hydrogen, optionally substituted $C_1$-$C_5$-alkanoyl or optionally substituted benzoyl, phenylacetyl or phenylpropionyl;

$R^3$ is hydroxy; optionally substituted $C_1$-$C_5$ alkanoyloxy; optionally substituted benzoyloxy, phenylacetoxy or phenoxyacetoxy; or —O— [structure] —OH;
(mycarosyloxy)

[structure 2]

wherein
$Q^1$ is $Q^2O$— [structure] —O—

$Q^2$ is hydrogen or a hydroxyl-protecting group;
$Q^3$ is hydrogen or iodo; and
R and $R^2$ are as defined in formula 1;
and to the acid addition salts of these compounds.

The compounds of this invention are useful as antibiotics and/or as intermediates to antibiotics. This invention also relates to pharmaceutical compositions comprising these compounds and to methods of treatment wherein these compounds or compositions are administered to obtain an antibiotic effect or to enhance growth promotion in animals.

DETAILED DESCRIPTION OF THE INVENTION

This invention relates to new antibiotics. In particular, this invention relates to a group of C-20-modified derivatives of the macrolide antibiotics tylosin, desmycosin, macrocin, lactenocin, 2'''-O-demethylmacrocin (DOMM) and 2''-O-demethyllactenocin (DOML) and to the acid addition salts of these derivatives. This invention also relates to methods of treating certain infections with, methods of promoting growth in animals with, and pharmaceutical compositions comprising the specified derivatives and their pharmaceutically acceptable acid addition salts.

New, improved antibiotics are continually in demand. In addition to antibiotics which are useful for treating human diseases, improved antibiotics are also needed in the veterinary field. Increased potency, expanded spectrum of bacterial inhibition, increased in vivo efficacy, and improved pharmaceutical properties (such as greater oral absorption, higher blood or tissue concentrations, longer body half life, and more advantageous rate or route of excretion and rate or pattern of metabolism) are some of the goals for improved antibiotics.

Unfortunately, conversion of tylosin-like macrolides to derivatives having improved properties has not been very successful. A large number of derivatives have been made, but the utility of these derivatives has been similar to, or less than, that of the parent compound.

Unexpectedly, we have now discovered that modification of the C-20 aldehyde group via reductive amination to a C-20-dihydro-deoxy-(cyclic tertiary amino group) has resulted in derivatives with significantly increased activity.

One group of novel macrolides of this invention are compounds of formula 1:

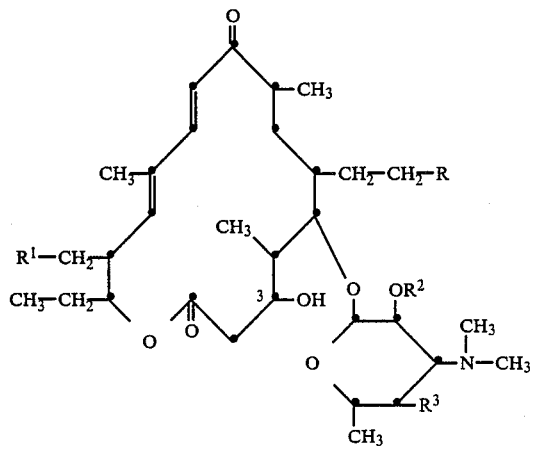

wherein
R is a saturated or unsaturated secondary amino group of the formula

in which the nitrogen atom is part of an otherwise carbocyclic ring system selected from a monocyclic ring containing from 5 to 16 ring atoms or a bicyclic or tricyclic ring system containing from 8 to 20 ring atoms wherein one or more of the carbon atoms may be substituted by $C_1-C_4$ alkyl, $C_2-C_4$ alkenyl, $C_2-C_4$ alkynyl, $C_1-C_4$ alkoxy, $C_1-C_4$ alkoxycarbonyl, hydroxyl, $C_1-C_4$ alkanoyloxy, halo, halo-$C_1-C_4$ alkyl, $-N(C_1-C_4 \text{ alkyl})_2$, $-N(CH_2)_m$,

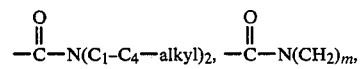

cyano, ethylenedioxy, benzyl, phenyl or phenyl substituted by from 1 to 3 substituents selected from nitro, halo, $C_1-C_4$-alkyl, $C_1-C_4$ alkoxy, hydroxy, amino, or mono- or di-($C_1-C_4$ alkyl)amino;
m is an integer from 4 through 7;
$R^1$ is

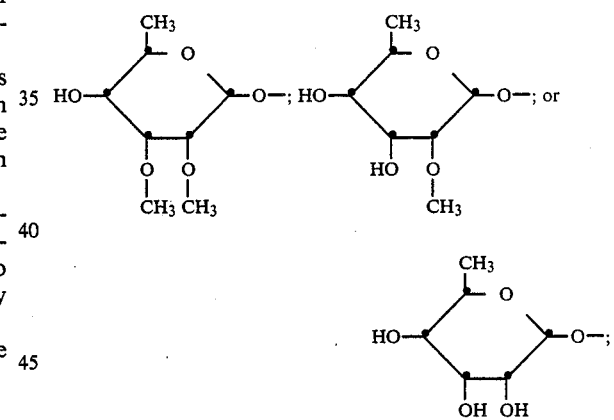

$R^2$ is hydrogen, optionally substituted $C_1-C_5$-alkanoyl or optionally substituted benzoyl, phenylacetyl or phenylpropionyl;

$R^3$ is hydroxy; optionally substituted $C_1-C_5$-alkanoyloxy; optionally substituted benzoyloxy, phenylacetoxy or phenoxyacetoxy; or

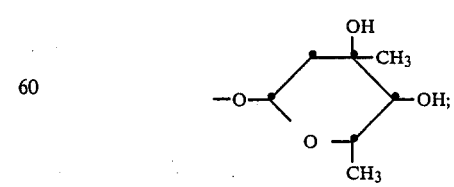

and the acid addition salts of these compounds.

Another group of novel macrolides of this invention are compounds of formula 2:

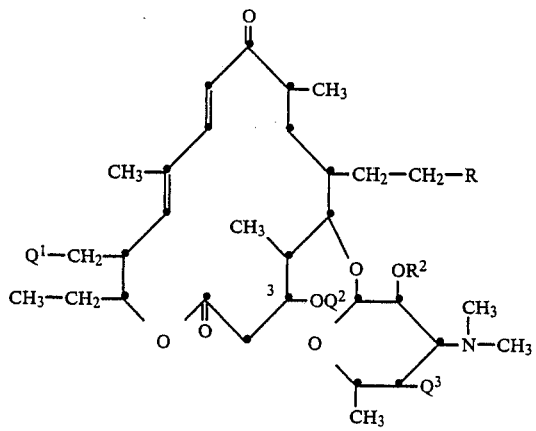

wherein
Q¹ is

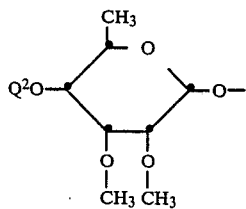

Q² is hydrogen or a hydroxyl-protecting group;
Q³ is hydrogen or iodo; and
R and R² are as defined in formula 1;
and to the acid addition salts of these compounds.

Although no stereochemical assignments are indicated in the structures given herein, the stereochemistry is identical to that of the antibiotics from which the compounds are prepared, e.g. tylosin.

When R is unsaturated, representative groups are 1,2,3,6-tetrahydropyridin-1-yl; 1,2,3,4-tetrahydroquinolin-1-yl; 1,2,3,4-tetrahydroisoquinolin-2-yl; indol-1-yl; isoindol-2-yl; indolin-1-yl; isoindolin-2-yl; 2,3,4,5-tetrahydro-1H-1-benzazepin-1-yl; 2,3,4,5-tetrahydro-1H-2-benzazepin-2-yl; 2,3,4,5-tetrahydro-1H-3-benzazepin-3-yl; pyrrol-1-yl; 1H-azepin-1-yl; carbazol-9-yl; acridin-10-yl; and acridin-9-one-10-yl.

When R is a saturated monocyclic ring, representative groups include pyrrolidin-1-yl, piperidin-1-yl, hexahydroazepin-1-yl, octahydroazocin-1-yl, octahydro-1H-azonin-1-yl, azacyclotridecan-1-yl and the like.

When R is a saturated bicyclic or tricyclic ring, representative groups include decahydroquinolin-1-yl; decahydroisoquinolin-2-yl; decahydrocyclohepta[b]pyrrol-1-yl; decahydrocyclohepta[c]pyrrol-2-yl; decahydrocyclopent[c]azepin-2-yl; decahydrocyclopent[d]azepin-3-yl; an azabicycloheptanyl group such as 3-azabicyclo[3.2.0]heptan-3-yl; an azabicyclooctanyl group such as 6-azabicyclo[3.2.1]octan-6-yl; an azabicyclononanyl group such as 3-azabicyclo[3.2.2]nonan-3-yl; an azabicyclodecanyl group such as 4-azabicyclo[5.3.0]decan-4-yl; an azatricyclo group such as 2-azatricyclo[6.2.2.2$^{3,6}$]tetradecan-2-yl or dodecahydrocarbazol-9-yl; and a spiro-fused system such as 1-azaspiro[4.5]decan-1-yl.

Representative groups when R has one or more substituents on the carbon atoms of the ring system include 1,3,3-trimethyl-6-azabicyclo[3.2.1]octan-6-yl; 4-piperidinopiperidin-1-yl; 3,3,5-trimethylhexahydroazepin-1-yl; 4-phenylpiperidin-1-yl; 3,5-dimethylpiperidin-1-yl; 3-(N,N-diethylcarbamoyl)piperidin-1-yl; and the like.

The term $C_1$–$C_4$ means a hydrocarbon group containing from one to four carbon atoms which can be straight, branched, or cyclic. By alkenyl and alkynyl are meant a hydrocarbon group containing a double or triple bond, respectively. The term "$C_1$–$C_5$-alkanoyl" as used herein refers to an acyl moiety derived from a carboxylic acid containing from one to five carbon atoms. When optionally substituted, the alkyl group can bear one to three halo substituents. Halo substituents are selected from the group consisting of Cl, Br and F. Acetyl, chloroacetyl, trichloroacetyl, trifluoroacetyl, propionyl, n-butyryl, isobutyryl, n-valeryl, and isovaleryl are examples of such groups. The term "$C_1$–$C_5$-alkanoyloxy" refers to the corresponding acyloxy moiety.

The terms "optionally substituted benzoyl, phenylacetyl or phenylpropionyl" and "optionally subtituted benzoyloxy, phenylacetoxy or phenoxyacetoxy" mean that the phenyl portion of the moiety is optionally substituted by from one to five halo or methyl groups or by from one to two methoxyl, nitro or hydroxyl groups.

The term "hydroxyl-protecting group" refers to a substituent which is not removed under the reaction conditions but which can be readily removed after the reaction has been completed to liberate the original hydroxyl group. Hydroxyl-protecting groups are well known in the art (see, for example, T. W. Greene, "Protective Groups in Organic Synthesis", Wiley-Interscience, 1981, pp. 10–86). One especially suitable hydroxyl-protecting group is the tetrahydropyranyl group.

The C-20-modified macrolide derivatives of this invention are prepared from the group of macrolide antibiotics which includes tylosin, relomycin, desmycosin, 20-dihydrodesmycosin, macrocin, 20-dihydromacrocin, 2'''-O-demethylmacrocin (DOMM), 20-dihydro-DOMM, lactenocin, 20-dihydro-lactenocin, 2'''-O-demethyllactenocin (DOML) and 20-dihydro-DOML.

Tylosin and desmycosin are described by R. L. Hamill et al. in U.S. Pat. No. 3,178,341, issued Apr. 13, 1965. Macrocin and lactenocin are described by Hamill et al. in U.S. Pat. No. 3,326,759, issued June 20, 1967. DOMM, dihydro-DOMM, DOML and dihydro-DOML are antibiotics described by Richard H. Baltz, Gene M. Wild, and Eugene T. Seno in U.S. Pat. No. 4,385,116, issued May 24, 1983. The structures of these antibiotics are shown in formulas 3–14:

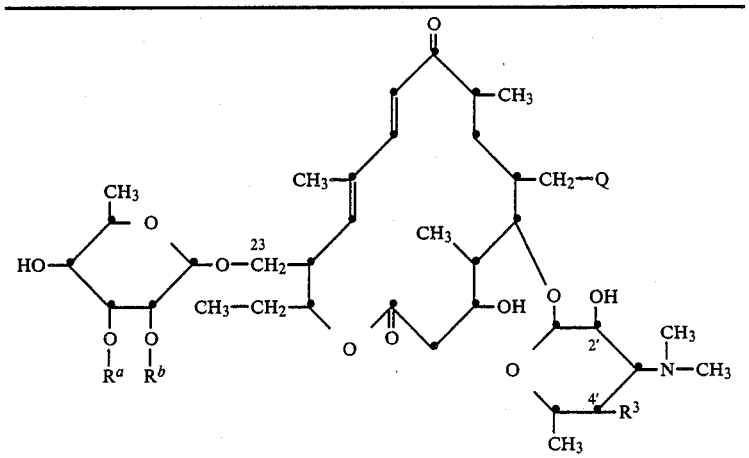

| | Q | $R^a$ | $R^b$ | $R^3$ |
|---|---|---|---|---|
| 3 (tylosin): | —CHO | —CH₃ | —CH₃ | —O—mycarosyl |
| 4 (relomycin): | —CH₂OH | —CH₃ | —CH₃ | —O—mycarosyl |
| 5 (desmycosin): | —CHO | —CH₃ | —CH₃ | —OH |
| 6 (dihydrodesmycosin): | —CH₂OH | —CH₃ | —CH₃ | —OH |
| 7 (macrocin): | —CHO | H | —CH₃ | —O—mycarosyl |
| 8 (dihydromacrocin): | —CH₂OH | H | —CH₃ | —O—mycarosyl |
| 9 (lactenocin): | —CHO | H | —CH₃ | —OH |
| 10 (dihydrolactenocin): | —CH₂OH | H | —CH₃ | —OH |
| 11 (DOMM): | —CHO | H | H | —O—mycarosyl |
| 12 (dihydro-DOMM): | —CH₂OH | H | H | —O—mycarosyl |
| 13 (DOML): | —CHO | H | H | —OH |
| 14 (dihydro-DOML): | —CH₂OH | H | H | —OH |

Preparation of the C-20-modified derivatives of this invention involves, in a formal sense, reductive amination of the C-20 aldehyde group of tylosin, desmycosin, macrocin, lactenocin, DOMM or DOML. This can be accomplished by two methods.

METHOD 1

In this method, the aldehyde group of compound 3, 5, 7, 9, 11, or 13 is first reduced to give the corresponding 20-dihydro compounds, i.e. the compounds of formulas 4, 6, 8, 10, 12, and 14. The C-20 hydroxyl group in these compounds is then converted to a leaving group suitable for displacement reactions by one of two methods. In one method the C-20 hydroxyl group is converted to the trifluoromethanesulfonyloxy (triflate) group, which may be further converted to another leaving group such as iodo, if desired. In the other method, which can only be used with desmycosin, lactenocin and DOML, the iodo derivative is directly formed by addition of iodine (which may be dissolved in a suitable solvent such as dimethylformamide) to a solution of the 20-dihydro derivative and triphenylphosphine under nitrogen.

The leaving group at C-20 (iodo, triflate, etc.) is then displaced by reaction with the appropriate amine in a suitable solvent, such as acetonitrile, until the desired 20-modified derivative is formed.

METHOD 2

In this method, the aldehyde group of compound 3, 5, 7, 9, 11 or 13 is reacted directly with the corresponding amine in the presence of a suitable reducing agent in an appropriate solvent until the desired product is formed. Sodium cyanoborohydride and sodium borohydride are examples of suitable reducing agents, and anhydrous methanol is a useful solvent for this reaction. The reaction may be carried out under a nitrogen atmosphere, but this is usually not required.

The C-20-modified derivatives of desmycosin, lactenocin and DOML can also be prepared by acidic hydrolysis of mycarose from the corresponding C-20-modified derivatives of tylosin, macrocin and DOMM, respectively. Procedures for the acidic hydrolysis of mycarose from tylosin and macrocin to form desmycosin and lactenocin, respectively, are well known. DOMM is hydrolyzed in a similar manner to form DOML.

The 4'-deoxy derivatives of this invention, i.e. the compounds of formula 2 wherein $Q^3$=H, are readily prepared by procedures analogous to those described supra, using 4'-deoxydesmycosin as starting material. The starting material can be prepared via procedures outlined in *J. Antibiotics* 34, 1381–1384 (1981). In many cases, the C-20-modified derivative of desmycosin can be converted to the C-20-modified 4'-deoxy analog by similar procedures.

The ester derivatives of the C-20-modified compounds of this invention are prepared by esterifying the appropriate C-20-modified derivative on the 2'- or 2' and 4'-hydroxyl groups by treatment with acylating agents, using standard methods well exemplified in the art. The preparation of 2'-O-ester derivatives of the C-20-modified derivatives is accomplished by procedures similar to those described by Baltz et al. in U.S. Pat. Nos. 4,321,361 and 4,321,362. 2',4'-Di-O-ester derivatives of C-20-modified derivatives may be prepared using procedures analogous to those described by Herbert A. Kirst in U.S. Pat. No. 4,401,660, issued Aug. 30, 1983, which is incorporated herein by reference.

The C-20-modified derivatives of this invention form salts, particularly acid addition salts. These acid addition salts are also useful as antibiotics and are a part of this invention. In another aspect, such salts are useful as intermediates, for example, the separating and purifying the derivatives. In addition, the salts have an improved solubility in water.

Representative suitable salts include those salts formed by standard reactions with both organic and inorganic acids such as, for example, sulfuric, hydrochloric, phosphoric, acetic, succinic, citric, lactic, maleic, fumaric, palmitic, cholic, pamoic, mucic, D-glutamic, d-camphoric, glutaric, glycolic, phthalic, tartaric, formic, lauric, stearic, salicylic, methanesulfonic, benzenesulfonic, sorbic, picric, benzoic, cinnamic, and like acids.

Pharmaceutically acceptable acid addition salts are an especially preferred group of salts of this invention.

Illustrative C-20-modified derivatives of this invention include the compounds listed in Tables I–VIII.

TABLE I

Illustrative C-20 Modified Derivatives of Tylosin[a]

| Compound No. | R |
|---|---|
| T1 | pyrrolidin-1-yl |
| T2 | piperidin-1-yl |
| T3 | 4-hydroxypiperidin-1-yl |
| T4 | 4-phenylpiperidin-1-yl |
| T5 | hexahydroazepin-1-yl |
| T6 | octahydroazocin-1-yl |
| T7 | octahydro-1H—azonin-1-yl |
| T8 | decahydroazecin-1-yl |
| T9 | azacycloundecan-1-yl |
| T10 | azacyclotridecan-1-yl |
| T11 | 1,2,3,4-tetrahydroquinolin-1-yl |
| T12 | 1,2,3,4-tetrahydroisoquinolin-2-yl |
| T13 | 3-azabicyclo[3.2.2]nonan-3-yl |
| T14 | 3,5-dimethylpiperidin-1-yl |
| T15 | cis-3,5-dimethylpiperidin-1-yl |
| T16 | trans-3,5-dimethylpiperidin-1-yl |

[a] $R^1 =$ 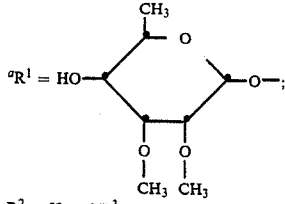 ; $R^2 =$ H; and $R^3 =$ mycarosyloxy

TABLE II

Illustrative C-20 Modified Derivatives of Desmycosin[a]

| Compound No. | R | $R^3$ or $Q^3$ |
|---|---|---|
| D1 | pyrrolidin-1-yl | OH |
| D1a | " | H |
| D2 | piperidin-1-yl | OH |
| D2a | " | H |
| D3 | 4-hydroxypiperidin-1-yl | OH |
| D3a | " | H |
| D4 | 4-phenylpiperidin-1-yl | OH |
| D4a | " | H |
| D5 | hexahydroazepin-1-yl | OH |
| D5a | " | H |
| D6 | octahydroazocin-1-yl | OH |
| D6a | " | H |
| D7 | octahydro-1H—azonin-1-yl | OH |
| D7a | " | H |
| D8 | decahydroazecin-1-yl | OH |
| D8a | " | H |
| D9 | azacycloundecan-1-yl | OH |
| D9a | " | H |
| D10 | azacyclotridecan-1-yl | OH |
| D10a | " | H |
| D11 | 1,2,3,4-tetrahydroquinolin-1-yl | OH |
| D11a | " | H |
| D12 | 1,2,3,4,-tetrahydroisoquinolin-2-yl | OH |
| D12a | " | H |
| D13 | 4-piperidinopiperidin-1-yl | OH |
| D13a | " | H |
| D14 | 3-azabicyclo[3.2.2.]nonan-3-yl | OH |
| D14a | " | H |
| D15 | 3-(N,N—diethylcarbamoyl)piperidin-1-yl | OH |
| D15a | " | H |
| D16 | 4-(N,N—dimethylamino)hexahydro-azepin-1-yl | OH |
| D16a | 4-(N,N—dimethylamino)hexahydro-azepin-1-yl | H |
| D17 | 2-azabicyclo[2.2.2]octan-2-yl | OH |
| D17a | " | H |
| D18 | decahydrocyclopent[d]azepin-3-yl | OH |
| D18a | " | H |
| D19 | 1-azaspiro[4.5]decan-1-yl | OH |
| D19a | " | H |
| D20 | decahydroquinolin-1-yl | OH |
| D20a | " | H |
| D21 | 1,3,3-trimethyl-6-azabicyclo-[3.2.1]octan-6-yl | OH |
| D21a | 1,3,3,-trimethyl-6-azabicyclo-[3.2.1]octan-6-yl | H |
| D22 | 1,2,3,6-tetrahydropyridin-1-yl | OH |
| D22a | " | H |
| D23 | 3,3,5-trimeythlhexahydroazepin-1-yl (isomer 1) | OH |
| D23a | 3,3,5-trimethylhexahydroazepin-1-yl (isomer 1) | H |
| D24 | 3,3,5-trimethylhexahydroazepin-1-yl (isomer 2) | OH |
| D24a | 3,3,5-trimethylhexahydroazepin-1-yl (isomer 2) | H |
| D25 | dodecahydrocarbazol-9-yl | OH |
| D25a | " | H |
| D26 | 4-phenyl-1,2,3,6-tetrahydropyridin-1-yl | OH |
| D26a | " | H |
| D27 | 4-benzyl-piperidin-1-yl | OH |
| D27a | " | H |
| D28 | 4-(ethylenedioxy)-piperidin-1-yl | OH |
| D28a | " | H |
| D29 | decahydroisoquinolin-2-yl | OH |
| D29a | " | H |
| D30 | 7-azabicyclo[2.2.1]heptan-7-yl | OH |
| D30a | " | H |
| D31 | Pyrrol-1-yl | OH |
| D31a | " | H |
| D32 | Carbazol-9-yl | OH |
| D32a | " | H |
| D33 | 3,5-dimethylpiperidin-1-yl | OH |
| D33a | " | H |
| D34 | cis-3,5-dimethylpiperidin-1-yl | OH |
| D34a | " | H |
| D35 | trans-3,5-dimethylpiperidin-1-yl | OH |
| D35a | " | H |
| D36 | 3-methylpiperidin-1-yl | OH |
| D37 | 3,4-dimethoxypiperidin-1-yl | OH |
| D38 | 2-ethylpiperidin-1-yl | OH |
| D39 | 4,4-dimethylpiperidin-1-yl | OH |
| D40 | 3,3-dimethylpiperidin-1-yl | OH |
| D41 | 2,6-dimethylpiperidin-1-yl | OH |
| D42 | 2,3-dihydroindol-1-yl | OH |
| D43 | 3-azaspiro[5.5]undecan-3-yl | OH |
| D44 | octahydroindol-1-yl | OH |
| D45 | octahydroisoindol-2-yl | OH |
| D46 | 3-azabicyclo[3.2.1]octan-3-yl | OH |
| D47 | 1,8,8-trimethyl-3-azabicuclo- | OH |

TABLE II-continued

Illustrative C-20 Modified
Derivatives of Desmycosin[a]

| Compound No. | R | R[3] or Q[3] |
|---|---|---|
| | [3.2.1]octan-3-yl | |

[a]$R^1/Q^1$ = HO— ...; $R^2$ = H

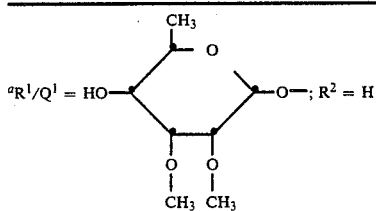

TABLE III

Illustrative C-20 Modified
Derivatives of Macrocin[a]

| Compound No. | R |
|---|---|
| M1 | pyrrolidin-1-yl |
| M2 | 4-phenylpiperidin-1-yl |
| M3 | hexahydroazepin-1-yl |
| M4 | octahydroazocin-1-yl |
| M5 | octahydro-1H—azonin-1-yl |
| M6 | azacyclotridecan-1-yl |
| M7 | 1,2,3,4-tetrahydroisoquinolin-2-yl |
| M8 | 3-azabicyclo[3.2.2]nonan-3-yl |
| M9 | 3,5-dimethylpiperidin-1-yl |
| M10 | cis-3,5-dimethylpiperidin-1-yl |
| M11 | trans-3,5-dimethylpiperidin-1-yl |

[a]$R^1$ = HO— ...

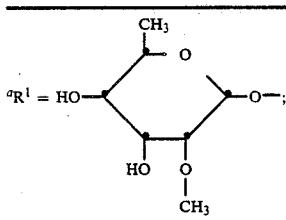

$R^2$ = H; and $R^3$ = mycarosyloxy

TABLE IV

Illustrative C-20 Modified
Derivatives of Lactenocin[a]

| Compound No. | R |
|---|---|
| L1 | pyrrolidin-1-yl |
| L2 | piperidin-1-yl |
| L3 | 4-phenylpiperidin-1-yl |
| L4 | hexahydroazepin-1-yl |
| L5 | octahydroazocin-1-yl |
| L6 | octahydro-1H—azonin-1-yl |
| L7 | azacyclotridecan-1-yl |
| L8 | 1,2,3,4-tetrahydroisoquinolin-2-yl |
| L9 | 3-azabicyclo[3.2.2]nonan-3-yl |
| L10 | 1,3,3-trimethyl-6-azabicyclo[3.2.1]-octan-6-yl |
| L11 | 3,5-dimethylpiperidin-1-yl |
| L12 | cis-3,5-dimethylpiperidin-1-yl |
| L13 | trans-3,5-dimethylpiperidin-1-yl |

[a]$R^1$ = HO— ...

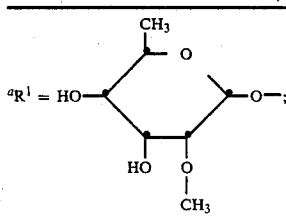

$R^2$ = H; and $R^3$ = OH

TABLE V

Illustrative C-20-Modified
Derivatives of DOMM[a]

| Compound No. | R |
|---|---|
| C1 | pyrrolidin-1-yl |
| C2 | 4-phenylpiperidin-1-yl |
| C3 | hexahydroazepin-1-yl |
| C4 | octahydroazocin-1-yl |
| C5 | azacyclotridecan-1-yl |
| C6 | 3,5-dimethylpiperidin-1-yl |

[a]$R^1$ = HO— ...;

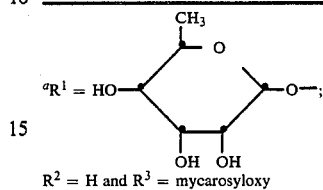

$R^2$ = H and $R^3$ = mycarosyloxy

TABLE VI

Illustrative C-20-Modified
Derivatives of DOML[a]

| Compound No. | R |
|---|---|
| N1 | pyrrolidin-1-yl |
| N2 | 4-phenylpiperidin-1-yl |
| N3 | hexahydroazepin-1-yl |
| N4 | octahydroazocin-1-yl |
| N5 | octahydro-1H—azonin-1-yl |
| N6 | azacyclotridecan-1-yl |
| N7 | 1,2,3,4-tetrahydroquinolin-1-yl |
| N8 | 3,5-dimethylpiperidin-1-yl |

[a]$R^1$ = HO— ...;

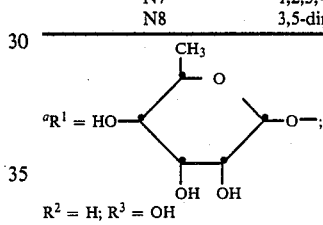

$R^2$ = H; $R^3$ = OH

TABLE VII

Illustrative C-20-Modified
Ester Derivatives of Tylosin[a]

| Compound No. | R | $R^2$ (2')[b] |
|---|---|---|
| E1 | hexahydroazepin-1-yl | propionyl |
| E2 | octahydroazocin-1-yl | propionyl |
| E3 | piperidin-1-yl | acetyl |
| E4 | 3,5-dimethylpiperidin-1-yl | acetyl |

[a]$R^1$ = HO— ...—O—, $R^3$ = mycarosyloxy

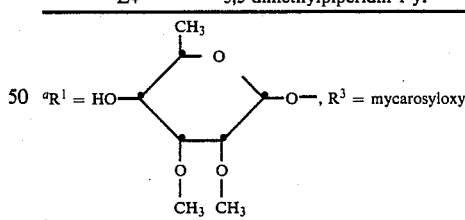

[b]position number of esterified hydroxyl group in parentheses

TABLE VIII

Illustrative C-20-Modified
Ester Derivatives of Desmycosin[a]

| Compound No. | R | $R^2$ (2')[b] | $R^3$ (4')[b] |
|---|---|---|---|
| E42 | hexahydroazepin-1-yl | propionyl | OH |
| E5 | hexahydroazepin-1-yl | propionyl | propionyloxy |
| E6 | octahydroazocin-1-yl | acetyl | OH |
| E7 | octahydroazocin-1-yl | acetyl | acetoxy |
| E8 | piperidin-1-yl | propionyl | OH |
| E9 | 3,5-dimethylpiperidin-1-yl | acetyl | OH |
| E10 | 3,5-dimethylpiperidin-1-yl | acetyl | acetoxy |

TABLE VIII-continued

Illustrative C-20-Modified Ester Derivatives of Desmycosin[a]

| Compound No. | R | R[2] (2')[b] | R[3] (4')[b] |
|---|---|---|---|
| E11 | cis-3,5-dimethylpiperidin-1-yl | acetyl | OH |
| E12 | cis-3,5-dimethylpiperidin-1-yl | acetyl | acetoxy |
| E13 | trans-3,5-dimethylpiperidin-1-yl | acetyl | OH |
| E14 | trans-3,5-dimethylpiperidin-1-yl | acetyl | acetoxy |

[a]R[1] = 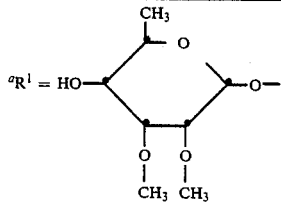

[b]position number of esterified hydroxyl group in parentheses

The derivatives of this invention inhibit the growth of pathogenic bacteria, especially gram-positive bacteria, Mycoplasma species and gram-negative bacteria such as Pasteurella species. The derivatives are particularly useful against Pasteurella species such as *P. multocida* and *P. hemolytica* and against Mycoplasma species such as *M. gallisepticum* and *M. hyopneumoniae* (the causative agent of mycoplasmal pneumonia in swine).

The minimal inhibitory concentrations (MIC's) at which illustrative compounds inhibit certain bacteria are given in Tables IX and X. The MIC's in Table IX were determined by standard agar-dilution assays. The MIC's in Table X were obtained using conventional broth-dilution microtiter tests.

TABLE IX

Antibiotic Activity C-20 Modified Derivatives[a]

| Test Organism | D1 | D4 | D5 | D5a | D6 | D10 | D14 | M3 | L5 |
|---|---|---|---|---|---|---|---|---|---|
| *Staphyloccus aureus* X1.1 | 2 | 0.5 | 0.5 | 0.5 | 0.5 | 0.25 | 0.25 | 4 | 1 |
| *Staphylococcus aureus* V41[c] | 2 | 0.5 | 0.5 | 0.5 | 0.5 | 0.25 | 0.25 | 8 | 1 |
| *Staphylococcus aureus* X400[d] | 2 | 0.5 | 1 | 1 | 0.5 | 0.25 | 0.5 | 32 | 2 |
| *Staphylococcus aureus* S13E | 2 | 0.5 | 0.25 | 0.5 | 0.5 | 0.25 | 0.25 | 8 | 1 |
| *Staphylococcus epidermis* EPI1 | 2 | 0.5 | 0.5 | 0.5 | 05 | 0.25 | 0.5 | 8 | 1 |
| *Staphylococcus epidermidis* 222 | 1 | 0.25 | 0.12 | 0.25 | 0.25 | 0.12 | 0.12 | 2 | 0.5 |
| *Streptococcus pyogenes* C203 | 1 | 0.25 | 0.5 | 0.25 | 0.5 | NT[i] | NT | 4 | 0.5 |
| *Streptococcus pneumoniae* Park I | 0.5 | 0.25 | 0.5 | 0.25 | 0.5 | 0.25 | 0.5 | 2 | 0.5 |
| Streptococcus Group D X66 | 32 | 1 | 8 | 2 | 4 | 4 | 4 | — | 16 |
| Streptococcus Group D 2041 | 16 | 2[h] | 8 | 2 | 8[h] | 4 | 4 | — | 16[h] |
| *Haemophilus influenzae* C.L.[e] | 16 | 8 | 16 | 8 | 16 | 4 | 4 | 128 | 32 |
| *Haemophilus influenzae* 76[f] | 16 | 8 | 128 | 8 | 16 | 8 | 8 | 128 | 6 |
| *Echerichia coli* N10 | —[g] | 64 | 128 | 64 | 64 | 32 | 32 | — | — |
| *Escherichia coli* EC14 | — | 64 | 4 | 128 | 64 | 64 | 32 | — | — |
| *Escherichia coli* TEM | 128 | 32 | 8 | 8 | 16 | 8 | 16 | — | 16 |
| Klebsiella X26 | 16 | 32 | —[g] | 8 | 16 | 16 | 8 | — | 16 |

| Test Organism | M4 | L4 | T6 | T13 | D2 | D3 | D7 | D11 | D12 |
|---|---|---|---|---|---|---|---|---|---|
| *Staphyloccus aureus* X1.1 | 4 | 2 | 4 | 4 | 0.5 | 8 | 0.5 | 0.5 | 0.5 |
| *Staphylococcus aureus* V41[c] | 4 | 2 | 4 | 4 | 0.5 | 8 | 0.5 | 0.5 | 0.5 |
| *Staphylococcus aureus* X400[d] | 8 | 2 | 8 | 8 | 1 | 16 | 0.5 | 0.5 | 0.5 |
| *Staphylococcus aureus* S13E | 4 | 2 | 4 | 4 | 0.5 | 8 | 0.5 | 0.5 | 0.5 |
| *Staphylococcus epidermis* EPI1 | 4 | 2 | 4 | 4 | 1 | 8 | 0.5 | 0.5 | 0.5 |
| *Staphylococcus epidermidis* 222 | 2 | 1 | 2 | 2 | 0.5 | 4 | 0.25 | 0.25 | 0.25 |
| *Streptococcus pyogenes* C203 | 2 | 1 | 2 | 4 | 0.25 | 1 | 0.06 | 0.5 | 0.5 |
| *Streptococcus pneumoniae* Park I | 32 | 8 | 8 | 16 | 0.25 | 8 | 0.5 | 2 | 1 |
| Streptococcus Group D X66 | — | 32 | — | 128 | 16 | 128 | 4 | 8 | 4 |
| Streptococcus Group D 2041 | — | 16 | — | — | 16 | 32 | 8 | 8 | 8 |
| *Haemophilus influenzae* C.L.[e] | 128 | 16 | 64 | 128 | 16 | 64 | 16 | 64 | 16 |
| *Haemophilus influenzae* 76[f] | 128 | 16 | — | 128 | 16 | 64 | 16 | 8 | 8 |
| *Echerichia coli* N10 | — | — | — | — | — | — | 64 | — | — |
| *Escherichia coli* EC14 | — | — | — | — | — | — | 64 | — | 128 |
| *Escherichia coli* TEM | — | — | — | — | 16 | — | 16 | — | 64 |
| Klebsiella X26 | — | 16 | — | — | 16 | 64 | — | — | 32 |

| Test Organism | D13 | D15 | D19 | D20 | D21 | D22 | D23 | D24 | D25 |
|---|---|---|---|---|---|---|---|---|---|
| *Staphylococcus aureus* X1.1 | 0.5 | 2 | 1 | 0.5 | 1 | 1 | 0.5 | 0.5 | 0.5 |
| *Staphylococcus aureus* V41[c] | 1 | 2 | 1 | 0.5 | 1 | 0.5 | 0.5 | 0.5 | 0.5 |
| *Staphylococcus aureus* X400[d] | 1 | 4 | 1 | 0.5 | 1 | 1 | 1 | 1 | 1 |
| *Staphylococcus aureus* S13E | 1 | 2 | 1 | 0.5 | 1 | 0.5 | 0.5 | 0.5 | 0.5 |
| *Staphylococcus epidermidis* EPI1 | 1 | 2 | 1 | 0.5 | 1 | 0.5 | 0.5 | 0.5 | 0.5 |
| *Staphylococcus epidermidis* 222 | 0.25 | 1 | 0.25 | 0.25 | 0.5 | 0.25 | 0.5 | 0.25 | 0.25 |
| *Sreptococcus pyogenes* C203 | 2 | 0.5 | 0.5 | 0.25 | 0.5 | 0.25 | 0.5 | 0.25 | 0.25 |
| *Streptococcus pneumoniae* Park I | 2 | 1 | 0.25 | 0.12 | 0.5 | 1 | 0.5 | 1 | 0.5 |
| Streptococcus Group D X66 | 2 | 32 | 16 | 8 | 4 | 8 | 4 | 4 | 4 |
| Streptococcus Group D 2041 | 2 | 32 | 16 | 8 | 8 | 8 | 8 | 8 | 4 |
| *Haemophilus influenzae* C.L.[e] | 16 | 32 | 16 | 16 | 32 | 16 | 16 | 32 | 16 |
| *Haemophilus influenzae* 76[f] | 8 | 32 | 16 | 16 | 16 | 8 | 8 | 8 | 8 |
| *Escherichia coli* N10 | — | — | 128 | 128 | 64 | — | 64 | 64 | 128 |
| *Escherichia coli* EC14 | — | — | 128 | 128 | 64 | — | 64 | 64 | 128 |
| *Escherichia coli* TEM | — | 64 | 32 | 32 | 32 | 64 | 32 | 32 | 32 |
| Klebsiella X26 | 16 | 32 | 32 | 16 | 64 | 64 | 128 | 128 | 128 |

TABLE IX-continued

Antibiotic Activity C-20 Modified Derivatives[a]

| Test Organism | D26 | D27 | D28 | D29 | D34 | D40 | D41 | D42 | D |
|---|---|---|---|---|---|---|---|---|---|
| *Staphylococcus aureus* X1.1 | 0.5 | 1 | 2 | 0.5 | 1 | 0.5 | 8 | 05 | 1 |
| *Staphylococcus aureus* V41[c] | 0.5 | 1 | 2 | 0.5 | 1 | 0.5 | 8 | 0.25 | 1 |
| *Staphylococcus aureus* X400[d] | 0.5 | 1 | 4 | 0.5 | 1 | 0.5 | 8 | 0.5 | 1 |
| *Staphylococcus aureus* S13E | 0.5 | 1 | 2 | 0.5 | 0.5 | 0.5 | 8 | 0.5 | 1 |
| *Staphylococcus epidermidis* EPI1 | 0.5 | 1 | 2 | 0.5 | 0.5 | 0.5 | 8 | 0.5 | 0.5 |
| *Staphylococcus epidermidis* 222 | 0.25 | 0.25 | 1 | 0.125 | 0.25 | 0.25 | 2 | 0.25 | 0.5 |
| *Streptococcus pyogenes* C203 | 0.25 | 0.25 | 0.5 | 0.5 | 0.5 | 0.25 | 1 | 0.5 | 0.5 |
| *Streptococcus pneumoniae* Park I | 0.25 | 0.5 | 2 | 0.5 | 2 | 2 | 1 | 0.25 | 2 |
| Streptococcus Group D X66 | 1 | 2 | 8 | 2 | 4 | 4 | 32 | 2 | 8 |
| Streptococcus Group D 2041 | 2 | 4 | 8 | 8 | 8 | 8 | 32 | 2 | 16 |
| *Haemophilus influenzae* C.L.[e] | 32 | 32 | 32 | 4 | 16 | 4 | 64 | 16 | NT |
| *Haemophilus influenzae* 76[f] | 8 | 16 | 32 | 4 | 4 | 8 | 64 | 8 | NT |
| *Escherichia coli* N10 | 128 | 128 | — | 64 | 128 | 64 | — | — | NT |
| *Escherichia coli* EC14 | 128 | 128 | — | 64 | 128 | 64 | — | — | NT |
| *Escherichia coli* TEM | 32 | 32 | 64 | 16 | 32 | 16 | — | — | NT |
| Klebsiella X26 | 64 | 64 | 64 | 32 | 64 | 16 | 128 | 64 | — |

[a]MIC in mcg/ml
[b]Compound numbers from Tables I–IV
[c]Penicillin-resistant strain
[d]Methicillin-resistant strain
[e]Ampicillin-sensitive strain
[f]Ampicillin-resistant strain
[g]Not active at 128 mcg/ml, the highest level tested
[h]tested using predecessor Group D strain 9960
[i]Not tested

TABLE X

Antibiotic Activity of C-20 Modified Derivatives[a]

| Test Organism | D1 | D2 | D3 | D4 | D5 | D6 | D7 | D10 | D11 | D12 |
|---|---|---|---|---|---|---|---|---|---|---|
| *Staphylococcus aureus* | 0.78 | 0.78 | 12.5 | 0.39 | 1.56 | 0.78 | 1.56 | 0.39 | 1.56 | 1.56 |
| Streptococcus sp. 19F | 6.25 | 6.25 | 12.5 | 0.09 | 3.12 | 0.78 | 3.12 | 0.78 | 3.12 | 3.12 |
| *Pasteurella multocida* 17E[c] | 6.25 | 25 | 50 | 6.25 | 3.12 | 3.12 | 6.25 | 1.56 | 12.5 | 6.25 |
| *Pasteurella multocida* 60A[d] | 6.25 | 6.25 | 50 | 6.25 | 3.12 | 6.25 | 6.25 | 3.12 | 50 | 12.5 |
| *Pasteurella hemolytica* 22C | 6.25 | 3.12 | 50 | 6.25 | 1.56 | 1.56 | 3.12 | 1.56 | 25 | 3.12 |
| *Mycoplasma gallisepticum* 29C | 12.5 | 3.12 | 25 | 0.39 | 1.56 | 1.56 | 0.39 | 0.097 | ≦0.048 | ≦0.048 |
| *Mycoplasma synoviae* 40A | 0.39 | 0.78 | 6.25 | <0.05 | 0.39 | 0.78 | 0.39 | ≦0.048 | 0.78 | 0.39 |
| *Mycoplasma hyorhinis* 29E | 50 | >50 | 50 | 50 | 50 | 50 | 25 | 12.5 | 6.25 | 12.5 |
| *Mycoplasma hyopneumonie* S5972 | 12.5 | 12.5 | 6.25 | 0.78 | 1.56 | 1.56 | 1.56 | 0.78 | 1.56 | 3.12 |

| Test Organism | D13 | D14 | D15 | D19 | D20 | D21 | D22 | D23 | D24 | D25 |
|---|---|---|---|---|---|---|---|---|---|---|
| *Staphylococcus aureus* | 3.12 | 0.78 | 6.25 | 0.78 | 0.78 | 0.78 | 1.56 | 3.12 | 3.12 | 3.12 |
| Streptococcus sp. 19F | 6.25 | 1.56 | 12.5 | 3.12 | 3.12 | 1.56 | 3.12 | 1.56 | 3.12 | 3.12 |
| *Pasteurella multocida* 17E[c] | 12.5 | 3.12 | 12.5 | 3.12 | 3.12 | 3.12 | 12.5 | 6.25 | 12.5 | 12.5 |
| *Pasteurella multocida* 60A[d] | 12.5 | 3.12 | 12.5 | 3.12 | 3.12 | 3.12 | 12.5 | 12.5 | 6.25 | 12.5 |
| *Pasteurella hemolytica* 22C | 12.5 | 1.56 | 25 | 3.12 | 3.12 | 3.12 | 3.12 | 3.12 | 6.25 | 3.12 |
| *Mycoplasma gallisepticum* 29C | 6.25 | 1.56 | 3.12 | 1.56 | 0.78 | 1.56 | 0.78 | 0.097 | 0.39 | 0.39 |
| *Mycoplasma synoviae* 40A | 1.56 | 0.39 | 1.56 | 0.39 | 0.195 | 0.39 | 0.78 | 0.097 | 0.097 | 0.097 |
| *Mycoplasma hyorhinis* 29E | 50 | 50 | >50 | >50 | 50 | — | 25 | 6.25 | 25 | 12.5 |
| *Mycoplasma hyopneumoniae* S5972 | 3.12 | 0.78 | 3.12 | 3.12 | 0.78 | 0.195 | 1.56 | 0.78 | 0.78 | 0.39 |

| Test Organism | L5 | D26 | D27 | D28 | D5a | L4 | T6 | T13 | M3 | M4 |
|---|---|---|---|---|---|---|---|---|---|---|
| *Staphylococcus aureus* | 1.56 | 3.12 | 3.12 | 3.12 | 0.39 | 6.25 | 12.5 | 6.25 | 12.5 | 12.5 |
| Streptococcus sp. 19F | 0.78 | 0.78 | 0.78 | 3.12 | 0.78 | 6.25 | 50 | 50 | 50 | 12.5 |
| *Pasteurella multocida* 17E[c] | 6.25 | 6.25 | 6.25 | 6.25 | 6.25 | 12.5 | >50 | >50 | >50 | >50 |
| *Pasteurella multocida* 60A[d] | 12.5 | 12.5 | 12.5 | 25 | 3.12 | 12.5 | >50 | >50 | >50 | >50 |
| *Pasteurella hemolytica* 22C | 12.5 | 12.5 | 12.5 | 25 | 3.12 | 25 | 50 | 50 | 50 | >50 |
| *Mycoplasma gallisepticum* 29C | 6.25 | ≦0.048 | ≦0.048 | 0.097 | 0.78 | 12.5 | 3.12 | 1.56 | 6.25 | 3.12 |
| *Mycoplasma synoviae* 40A | 3.12 | 0.78 | ≦0.048 | 0.195 | 0.195 | 1.56 | 0.78 | 1.56 | 25 | 6.25 |
| *Mycoplasma hyorhinis* 29E | 50 | 25 | 25 | 25 | 3.12 | 50 | >50 | >50 | >50 | >50 |
| *Mycoplasma hyopneumoniae* S5972 | NT[e] | 0.78 | 0.39 | 1.56 | 0.195 | 1.56 | 12.5 | 25 | 12.5 | 6.25 |

| Test Organism | D29 | D34 | D41 | D42 | D43 | D44 | D46 |
|---|---|---|---|---|---|---|---|
| *Staphylococcus aureus* 19C | 1.56 | 3.12 | 6.25 | 0.78 | 1.56 | 3.12 | 3.12 |
| Streptococcus sp. 19F | 1.56 | 3.12 | 6.25 | 0.78 | 1.56 | 1.56 | 1.56 |
| *Pasteurella multocida* 17E[c] | 3.12 | 12.5 | 25 | 12.5 | 6.25 | 12.5 | 6.25 |
| *Pasteurella multocida* 60A[d] | 6.25 | 12.5 | 50 | 25 | 6.25 | 12.5 | 12.5 |
| *Pasteurella hemolytica* 22C | 6.25 | 6.25 | >50 | 50 | 6.25 | 12.5 | 6.25 |
| *Mycoplasma gallisepticum* 29C | 0.195 | 0.195 | 6.25 | 0.097 | 0.195 | 1.56 | 0.195 |

TABLE X-continued

Antibiotic Activity of C-20 Modified Derivatives[a]

| | | | | | | | |
|---|---|---|---|---|---|---|---|
| Mycoplasma synoviae 40A | <0.048 | 0.78 | 1.56 | 0.195 | <0.048 | 0.097 | 1.56 |
| Mycoplasma hyorhinis 29E | 6.25 | 12.5 | 50 | 3.12 | 25 | 50 | 25 |
| Mycoplasma hyopneumoniae S5972 | 0.195 | 0.78 | 3.12 | 0.097 | 0.78 | 0.39 | 3.12 |

[a]MIC in mcg/ml
[b]Compound numbers from Tables I–IV
[c]Bovine isolate
[d]Avian isolate
[e]Not tested The C-20 modified derivatives of this invention have shown in vivo antimicrobial activity against experimentally-induced infections in laboratory animals. When two doses of test compound were administered to mice experimentally infected with *S. pyogenes* C203, the activity observed was measured as an $ED_{50}$ value [effective dose in mg/kg to protect 50% of the test animals: see Warren Wick, et al., *J. Bacteriol.* 81, 233–235 (1961)]. $ED_{50}$ values observed for illustrative compounds are given in Table XI.

TABLE XI $ED_{50}$ Values of C-20-Modified Derivatives vs. *Streptococcus pyogenes* C203 in Mice[a]

| Test Compound[b] | Subcutaneous | Oral |
|---|---|---|
| D1 | 1.2 | >50 |
| D2 | 0.9 | 50 |
| D4 | 6.0 | 19 |
| D5 | 1.3 | 50 |
| D5a | 1.5 | 34 |
| D6 | 0.7 | 14 |
| D7 | 1.6 | 12 |
| D10 | <10 | 68 |
| D11 | 7.5 | 19 |
| D12 | 2.0 | <6.3 |
| D14 | 1.0 | 50 |
| D19 | 2.9 | 46 |
| D20 | 1.7 | 34 |
| D21 | 1.0 | 10 |
| D22 | 0.8 | 40 |
| D26 | 5.61 | 12.5 |
| D27 | 3.81 | 16.5 |
| D28 | 0.75 | 77 |
| D29 | 1.56 | 10.3 |
| D34 | <0.625 | 7.98 |
| D35 | 0.88 | 10.93 |
| D41 | 2.04 | >100 |
| D43 | 1.34 | 8 |
| D44 | 0.69 | 37.9 |
| D48 | 7.53 | 25 |
| L5 | 1.8 | 100 |
| M3 | >10 | >100 |
| T6 | >10 | 44 |
| T13 | >10 | 30 |

[a]mg/kg × 2; doses given 1 and 4 hours post-infection
[b]Compound numbers from Tables I–IV.

Many of the C-20 modified derivatives of this invention have also shown in vivo antibacterial activity against infections induced by gram-negative bacteria. Tables XII and XIII summarize the results of tests in which illustrative compounds were evaluated against a Pasteurella infection in one-day-old chicks. The compounds were administered parenterally or orally after challenge of the chicks with *Pasteurella multocida* (0.1 ml of a $10^{-4}$ dilution of a twenty-hour tryptose broth culture of an avian *P. multocida* given subcutaneously). In these tests, unless indicated otherwise, all non-medicated infected chicks died within 24 hours of Pasteurella challenge. In the tests summarized in Table XII, the compounds were administered by subcutaneous injection at a dosage of 30 mg/kg, 1 and 4 hours post-challenge of the chicks with *P. multocida*. In the tests summarized in Table XIII the compounds were administered in medicated drinking water (at a level of 2 g/gal) available from 4 to 20 hours prior to challenge of the chicks with *P. multocida* and during the 3-day test period.

TABLE XII

Activity of C-20-Modified Derivatives Administered Subcutaneously to *Pasteurella multocida*-Infected Chicks[a]

| Test Compound[b] | Number of Deaths/Number Treated |
|---|---|
| D1 | 0/10 |
| D2 | 0/10 |
| D4 | 9/10 |
| D5 | 0/10 |
| D6 | 0/10 |
| D7 | 3/10 |
| D10 | 10/10 |
| D11 | 10/10 |
| D12 | 9/10 |
| D14 | 2/10 |
| D19 | 0/10 |
| D21 | 7/10 |
| D22 | 0/10 |
| D23 | 8/10 |
| D24 | 2/10 |
| D25 | 0/10 |
| D26 | 10/10 |
| D27 | 8/10 |
| D28 | 0/10 |
| D34 | 3/10 |
| D45 | 0/10 |
| D47 | 0/10 |
| L5 | 0/10 |

[a]Administered subcutaneously; 30 mg/kg × 2
[b]Compound numbers from Tables II and IV

TABLE XIII

Activity of C-20-Modified Derivatives Administered Orally to *Pasteurella multocida*-Infected Chicks[a]

| Test Compound[b] | Number of Deaths/Number Treated |
|---|---|
| D1 | 9/10 |
| D2 | 5/10 |
| D4 | 6/10 |
| D5 | 2/10 |
| D6 | 1/10 |
| D7 | 2/10 |
| D11 | 8/10 |
| D12 | 8/10 |
| D14 | 0/10 |
| D19 | 3/10 |
| D20 | 0/10 |
| D21 | 3/10 |
| D22 | 5/10 |
| D23 | 4/10 |
| D25 | 7/10 |
| D28 | 7/10 |
| D34 | 3/10, 0/10, 1/10, 6/10 |
| D45 | 1/10 |
| D46 | 3/10 |
| D47 | 6/10 |

[a]Administered in the available drinking water at a concentration of 2 g/gal
[b]Compound numbers from Table II This invention also relates to methods of controlling infections caused by bacterial and mycoplasmal species. In carrying out the methods of this invention, an effective amount of a compound of formula 1 or 2 is administered parenterally or orally to an infected or susceptible warm-blooded animal. The compounds can also be administered by insufflation, i.e. by blowing the compound, in the form of a medicated dust, into an enclosed space or room wherein the animals or poultry are held. The animals or poultry breathe the medicated dust present in the air; the medicated dust is also taken into the body through the eyes (a process called intraocular injection).

The dose which is effective to control the infection will vary with the severity of the infection and the age, weight, and condition of the animal. The total dose required for protection parenterally will generally, however, be in the range of from about 0.1 to about 100 mg/kg and preferably will be in the range of from about 0.5 to about 50 mg/kg. The dose required for oral administration will generally be in the range of from about 1 to about 300 mg/kg and preferably will be in the range of from about 1 to about 100 mg/kg. Suitable dosage regimens can be constructed.

A special advantage of this invention is that certain of the compounds are effective when administered as a single injection. For example, a single injection of 20-dihydro-20-deoxy-(cis-3,5-dimethylpiperidin-1-yl)desmycosin provides prolonged measurable blood and tissue levels of the drug for as long as seven days.

Often the most practical way to administer the compounds is by formulation into the feed supply or drinking water. A variety of feeds, including the common dry feeds, liquid feeds, and pelleted feeds, may be used.

In another aspect, this invention relates to compositions useful for the control of infections caused by bacteria and Mycoplasma species. These compositions comprise a compound of formula 1 or 2 together with a suitable vehicle. Compositions may be formulated for parenteral or oral administration by methods recognized in the pharmaceutical art.

The methods of formulating drugs into animal feeds are well-known. A preferred method is to make a concentrated-drug premix which in turn is used to prepare medicated feeds. Typical premixes may contain from about 1 to about 200 grams of drug per pound of premix. Premixes may be either liquid or solid preparations.

The final formulation of feeds for animals or poultry will depend upon the amount of drug to be administered. The common methods of formulating, mixing, and pelleting feeds may be used to prepare feeds containing a compound of formula 1 or 2.

Effective injectable compositions containing these compounds may be in either suspension or solution form. In the preparation of suitable formulations it will be recognized that, in general, the water solubility of the acid addition salts is greater than that of the free bases. Similarly, the bases are more soluble in dilute acids or in acidic solutions than in neutral or basic solutions.

In the solution form the compound is dissolved in a physiologically acceptable vehicle. Such vehicles comprise a suitable solvent, preservatives such as benzyl alcohol, if needed, and buffers. Useful solvents include, for example, water and aqueous alcohols, glycols, and carbonate esters such as diethyl carbonate.

Injectable suspension compositions require a liquid suspending medium, with or without adjuvants, as a vehicle. The suspending medium can be, for example, aqueous polyvinylpyrrolidone, inert oils such as vegetable oils or highly refined mineral oils, or aqueous carboxymethylcellulose.

Suitable physiologically acceptable adjuvants are necessary to keep the compound suspended in suspension compositions. The adjuvants may be chosen from among thickeners such as carboxymethylcellulose, polyvinylpyrrolidone, gelatin, and the alginates. Many surfactants are also useful as suspending agents. Lecithin, alkylphenol polyethylene oxide adducts, naphthalenesulfonates, alkylbenzenesulfonates, and the polyoxyethylene sorbitan esters are useful suspending agents.

Many substances which affect the hydrophilicity, density, and surface tension of the liquid suspending medium can assist in making injectable suspensions in individual cases. For example, silicone antifoams, sorbitol, and sugars can be useful suspending agents.

In order to illustrate more fully the operation of this invention, the following examples are provided. In these examples the abbreviation "20-DH-DO" is used for the term "20-dihydro-20-deoxy".

PREPARATION 1

20-Dihydrotylosin (Relomycin)

A solution of tylosin base (30.0 g, 32.8 mmole) in 2-propanol (300 ml) and water (200 ml) was treated with sodium borohydride (315 mg, 8.2 mmole), portionwise, over a five-minute period. Thirty minutes after the addition was completed, the pH of the reaction solution was adjusted to 7.0 by the addition of 1N sulfuric acid solution. The neutralized solution was evaporated under vacuum to remove the 2-propanol; the aqueous solution remaining was treated with a saturated sodium bicarbonate solution (500 ml). The mixture was extracted with dichloromethane (3×300 ml), and the combined extracts were extracted with saturated sodium chloride solution (200 ml) and dried over sodium sulfate. Filtration followed by evaporation gave a glass which was broken up in n-hexane, collected on a filter and air-dried to yield 28.5 g (95%) of 20-dihydrotylosin.

PREPARATION 2

20-Dihydrodesmycosin

Desmycosin (10 g, 13 mmoles), dissolved in isopropanol:water (1:1, 175 ml), was stirred at room temperature while NaBH$_4$ (125 mg, 3.3 mmoles) was added. After ½ hour the pH of the reaction mixture was adjusted to 7.0 with 1N H$_2$SO$_4$. The alcohol was removed under reduced pressure. Saturated NaHCO$_3$ solution was added to the aqueous solution, and the product was extracted into CH$_2$Cl$_2$. The organic layer was dried (Na$_2$SO$_4$), and solvent was removed under reduced pressure to give 9.65 g of 20-dihydrodesmycosin (12.5 mmoles, 96% yield) as a white foam.

PREPARATION 3

20-DH-DO-20-Iododesmycosin (Method 1)

20-Dihydrodesmycosin (2.0 g, 2.6 mmoles) and tetra n-butylammonium iodide (1.5 g, 3.9 mmoles) were dissolved in CH$_2$Cl$_2$ (30 ml) with s-collidine (0.6 ml, 4.5 mmoles) added. This solution was cooled at −78° C. under a nitrogen atmosphere and treated with trifluoromethanesulfonic anhydride (0.6 ml, 3.9 mmoles) dropwise by syringe. The reaction was stirred for 5 minutes at −78° C. then allowed to come to room temperature (about 30 minutes). Saturated NaHCO$_3$ solution was added, and the product was extracted with CH$_2$Cl$_2$. The organic layer was dried (Na$_2$SO$_4$) and evaporated to give a red oil which was purified by silica-gel flash chromatography, eluting initially with CH$_2$Cl$_2$ (400 ml) and then stepwise with CH$_2$Cl$_2$:CH$_3$OH solutions as follows: 98:2 (250 ml); 96:4 (500 ml) 95:5 (250 ml); 94:6 (750 ml) and 92:8 (250 ml). Fractions containing the desired product were identified by TLC, combined and evaporated to dryness to give 20-DH-DO-20-iododesmycosin (595 mg, 0.67 mmoles, 26% yield) as a white foam.

PREPARATION 4

20-DH-DO-20-Iododesmycosin (Method 2)

20-Dihydrodesmycosin (5.0 g, 6.5 mmoles) and triphenylphosphine (2.54 g, 9.70 mmoles) were dissolved in dimethylformamide (DMF) (10 ml). This mixture was stirred at room temperature under N$_2$ while iodine (2.46 g, 9.70 mmoles) in DMF (5 ml) was added dropwise. The reaction mixture was stirred for two hours and then poured into cold saturated NaHCO$_3$ solution. The product was extracted with CHCl$_3$ (two portions), and the combined CHCl$_3$ extracts were shaken with 0.1M sodium thiosulfate to remove unreacted iodine. The organic layer was dried (Na$_2$SO$_4$) and evaporated under reduced pressure to give a light yellow oil which was purified by silica-gel flash chromatography. The column was eluted initially with CH$_2$Cl$_2$ (500 ml) and then with 250 ml portions of CH$_2$Cl$_2$:CH$_3$OH mixtures as follows: 98:2; 96:4; 95:5; 94:6; 92:8; 88:12; and 86:14. Fractions containing the desired product were identified as in Preparation 3 and combined to give 1.78 g (2.0 mmoles, 31% yield) of 20-DH-DO-20-iododesmycosin as a white foam.

EXAMPLE 1

20-DH-DO-20-(Octahydroazocin-1-yl)desmycosin

20-DH-DO-20-Iododesmycosin (575 mg, 0.65 mmoles) was dissolved in acetonitrile (10 ml), and heptamethyleneimine (0.37 g, 0.41 ml, 3.3 mmoles) was added to this solution. The reaction was stirred at reflux for 1.5 hours. Volatiles were then removed under vacuum. The residue was dissolved in CH$_2$Cl$_2$ and extracted with saturated NaHCO$_3$ solution. The organic layer was dried (Na$_2$SO$_4$) and then evaporated under reduced pressure to give a light brown foam. This foam was purified by silica-gel flash chromatography, eluting with 250 ml each of the following CH$_2$Cl$_2$:CH$_3$OH mixtures: 98:2; 96:4; 94:6; 9:1; 88:12; 82:18; 65:35; 1:1; 1:3 and finally with 300 ml of CH$_3$OH. Fractions containing the desired product were identified by TLC, combined and evaporated to dryness to give 397 mg (0.46 mmoles, 71% yield) of 20-DH-DO-20-(octahydroazocin-1-yl)desmycosin as a white foam.

EXAMPLE 2

20-DH-DO-20-(Hexahydroazepin-1-yl)desmycosin

Desmycosin (10 g, 13 mmoles), dissolved in anhydrous methanol (100 ml), was added rapidly to a solution of NaBH$_3$CN (3.3 g, 52 mmoles) and hexamethyleneimine (6.5 g, 7.5 ml, 65 mmoles) in anhydrous methanol (50 ml) under N$_2$. The reaction mixture was stirred under N$_2$ at room temperature for about three hours and then was evaporated under reduced pressure. The resultant residue was dissolved in CH$_2$Cl$_2$ with just enough ethyl acetate to aid in dissolving the residue, and this solution was extracted with saturated NaHCO$_3$ solution. The organic layer was separated, dried (Na$_2$SO$_4$), and evaporated under reduced pressure to give a light yellow foam. This foam was purified by silica-gel flash chromatography, eluting initially with CH$_2$Cl$_2$ (1 L), then stepwise with 500-ml portions of CH$_2$Cl$_2$:CH$_3$OH mixtures as follows: 98:2; 96:4; 94:6; 92:8 and 9:1, and finally with CH$_2$Cl$_2$:CH$_3$OH:NH$_4$OH mixtures as follows: 90:10:0.5 (500 ml) and 75:25:0.5 (2 L). Fractions containing the desired product were identified by TLC, combined and evaporated to dryness to give 6.035 g (7.07 mmoles) of 20-DH-DO-20-(hexahydroazepin-1-yl)desmycosin as a white foam. Other fractions which contained impure product were combined, redissolved in CH$_2$Cl$_2$, extracted again with saturated NaHCO$_3$ solution, and purified as before, using a silica-gel column packed with CH$_2$Cl$_2$:CH$_3$OH (9:1) and eluted with CH$_2$Cl$_2$:CH$_3$OH:NH$_4$OH as follows: 90:10:0.5 (500 ml) and 80:20:0.5 (1 L) to give an additional 1.372 g (1.61 mmoles) of product. The total yield of 20-DH-DO-20-(hexahydroazepin-1-yl)desmycosin was 7.407 g (8.68 mmoles, 67%).

EXAMPLE 3

20-DH-DO-20-(4-Phenylpiperidin-1-yl)desmycosin

Desmycosin (1.5 g, 2 mmole) was dissolved in absolute methanol (60 ml) and treated with 4-phenylpiperidine (640 mg, 4 mmoles) in the presence of Linde 4A molecular sieves. After 0.5 hr, NaBH$_3$CN (500 mg, 8 mmoles) was added, and the mixture was stirred for 2.5 hr, at room temperature. The mixture was poured into saturated NaHCO$_3$ solution (200 ml) and extracted with CH$_2$Cl$_2$ (3×200 ml). The combined organic extracts were dried (Na$_2$SO$_4$), filtered and evaporated under reduced pressure. The residue (3.6 g) was purified by flash chromatography on silica gel, eluting with a gradient of 1 L. CH$_2$Cl$_2$ to 1 L. of MeOH:CH$_2$Cl$_2$ (5:95) and then with 1 L. of MeOH::CH$_2$Cl$_2$ (5:95). Fractions containing the desired product were located by TLC, combined and evaporated to dryness to yield 680 mg of 20-DH-DO-20-(4-phenylpiperidin-1-yl)desmycosin.

EXAMPLE 4

20-DH-DO-20-(Hexahydroazepin-1-yl)-4'-deoxydesmycosin

A solution of 4'-deoxydesmycosin (565 mg, 0.75 mmole) in methanol (15 ml) under argon was stirred with activated Linde 3A molecular sieves (2.2 g) for thirty minutes before hexamethyleneimine (0.25 ml, 2.25 mmole) was added. One hour later, sodium cyanoborohydride (141 mg, 2.25 mmole) was added to the reaction. After an additional 45 minutes, the reaction mixture was poured into saturated sodium bicarbonate solution and extracted with ethyl acetate. The combined organic extracts were shaken with saturated sodium chloride solution, dried over sodium sulfate, filtered and evaporated to yield 600 mg of crude product. This product was purified by preparative TLC on silica gel, eluting with dichloromethane/methanol/conc. ammonium hydroxide (90:15:2) to give 150 mg (24% yield) of 20-DH-DO-20-(hexahydroazepin-1-yl)-4'-deoxydesmycosin.

EXAMPLES 5–6

20-DH-DO-20-(Octahydroazocin-1-yl)desmycosin, prepared by the method of Example 2.

20-DH-DO-20-(Hexahydroazepin-1-yl)desmycosin, prepared by the method of Example 1.

EXAMPLE 7

20-DH-DO-20-(Octahydroazocin-1-yl)desmycosin (Method 3)

Desmycosin (4.0 g, 5.2 mmoles) was dissolved in absolute methanol (30 ml) and treated with heptamethyleneimine (1.2 g, 1.3 ml, 10.4 mmoles) in the presence of 3A molecular sieves. After the reaction mixture had been stirred for 1 hr at room temperature, a solution of $NaBH_4$ (60 mg, 1.6 mmoles) in absolute methanol (10 ml) was quickly added by pipette. The reaction mixture was stirred for 1.5 hr at room temperature, and then another 30 mg of $NaBH_4$ was added (one portion as the solid). The reaction mixture was stirred for another 75 min and then was filtered. The filtrate was evaporated under reduced pressure. The residue was dissolved in ethyl acetate (150 ml), and this solution was extracted with water (150 ml) and saturated $NaHCO_3$ solution (100 ml). The ethyl acetate solution was then extracted with pH 6.5, 0.5M $NaH_2PO_4$ buffer (150 ml). The buffer extract was evaporated under vacuum to remove residual ethyl acetate and then was rapidly stirred while 5N NaOH was slowly added, yielding a thick white precipitate. The white solid was removed by filtration, washed with a small amount of water, and dried to give 3.55 g of 20-DH-DO-20-(octahydroazocin-1-yl)desmycosin.

EXAMPLE 8

20-DH-DO-20-[1-Azaspiro[4.5]decan-1-yl]desmycosin

Desmycosin (5.0 g, 6.5 mmoles) was dissolved in absolute methanol (50 ml) and treated with 1-azaspiro[4.5]decane (1.36 g, 9.8 mmoles) in the presence of 3A molecular sieves. After 15 minutes, $NaBH_3CN$ (620 mg, 9.8 mmoles) was added, and the mixture was stirred for 17 hrs at room temperature. The reaction mixture was filtered, and the filtrate was evaporated under reduced pressure. The residue was dissolved in ethyl acetate, (300 ml) and extracted with water (300 ml and 100 ml). The product was then extracted from the ethyl acetate solution with pH 6.5, 0.5M $NaH_2PO_4$ buffer (300 ml and 100 ml). The phosphate buffer extracts were combined and evaporated under vacuum to remove residual ethyl acetate. The phosphate buffer solution was then rapidly stirred while 5N NaOH was slowly added, yielding a thick white precipitate. The white solid was removed by filtration, washed with water, and dried to give 20-DH-DO-20-[1-azaspiro[4.5]decan-1-yl]desmycosin (3.52 g).

EXAMPLE 9

20-DH-DO-20-(1,2,3,4-Tetrahydroquinolin-1-yl)desmycosin

Desmycosin (11.6 g, 15 mmol) was dissolved in dry methanol (100 ml), and 1,2,3,4-tetrahydroquinoline (3.8 ml 30 mmol) was added. After the mixture was stirred for 30 minutes at room temperature, sodium cyanoborohydride (1.25 g, 20 mmol) was added. The mixture was stirred overnight and then evaporated under reduced pressure. The residue was partitioned between ethyl acetate and water (100 ml each). The organic layer was then extracted sequentially with pH 6.5 aqueous phosphate buffer (100 ml) and pH 4.5 aqueous phosphate buffer (100 ml). The ethyl acetate layer was dried (sodium sulfate), filtered and evaporated; and the residue (4.6 g) was separated by chromatography on silica gel (Waters Prep 500). The column was eluted with a linear gradient of dichloromethane (4 L) and 5% methanol plus 0.5% conc. ammonium hydroxide in dichloromethane (4 L). Fractions containing the desired product were identified by TLC analysis, collected and evaporated to dryness to yield 3.4 g of the title compound.

EXAMPLE 10

20-DH-DO-20-(1,2,3,4-Tetrahydroisoquinolin-2-yl)desmycosin

Desmycosin (11.6 g, 15 mmol) was dissolved in dry methanol (100 ml), and 1,2,3,4-tetrahydroisoquinoline (3.8 ml, 30 mmol) was added. After the mixture was stirred for 30 minutes at room temperature, sodium cyanoborohydride (1.25 g, 20 mmol) was added. The mixture was stirred overnight and then was evaporated under reduced pressure. The residue was partitioned between ethyl acetate and water (150 ml each). The organic layer was then extracted sequentially with pH 6.5 phosphate buffer (100 ml) and pH 4.5 phosphate buffer (100 ml). After evaporation of the pH 4.5 buffer extract under reduced pressure to remove ethyl acetate, the pH was adjusted to 10 with 5N sodium hydroxide. The precipitate which formed was collected and air-dried to yield 5.6 g of the title compound.

EXAMPLE 11

20-DH-DO-20-(1,2,3,6-Tetrahydropyridin-1-yl)desmycosin

Desmycosin (11.6 g, 15 mmol) was dissolved in dry methanol (100 ml), and 1,2,3,6-tetrahydropyridine (2.8 ml, 30 mmol) was added. After the mixture was stirred for 30 minutes at room temperature, sodium cyanoborohydride (1.2 g, 20 mmol) was added. The mixture was stirred overnight and then was evaporated under reduced pressure. The residue was dissolved in ethyl acetate (150 ml). This solution was extracted with water (150 ml) and then with pH 6.5 aqueous phosphate buffer solution (2×100 ml). The buffer solutions were separately evaporated under reduced pressure to remove ethyl acetate and then adjusted to pH 10 with 5N sodium hydroxide. The precipitates which formed were collected by filtration and air-dried to yield 5.4 g (first extract) and 3.2 g (second extract) of the title compound.

EXAMPLES 12-32

The following compounds were prepared by the methods of Examples 1, 2, 7 or 8:
20-DH-DO-20-(3,3-dimethylpiperidin-1-yl)desmycosin
20-DH-DO-20-(octahydroazocin-1-yl)lactenocin
20-DH-DO-20-(pyrrolidin-1-yl)desmycosin
20-DH-DO-20-(azacyclotridecan-1-yl)desmycosin
20-DH-DO-20-(4-hydroxypiperidin-1-yl)desmycosin
20-DH-DO-20-(hexahydroazepin-1-yl)macrocin
20-DH-DO-20-[3-azabicyclo[3.2.2]nonan-3-yl]desmycosin
20-DH-DO-20-(piperidin-1-yl)desmycosin
20-DH-DO-20-[3-(N,N-diethylcarbamoyl)piperidin-1-yl]desmycosin
20-DH-DO-20-[(4-piperidino)piperidin-1-yl]desmycosin
20-DH-DO-20-(octahydro-1H-azonin-1-yl)desmycosin
20-DH-DO-20-(decahydroquinolin-1-yl)desmycosin
20-DH-DO-20-[1,3,3-trimethyl-6-azabicyclo[3.2.1]octan-6-yl]desmycosin 20-DH-DO-20-(dodecahydrocarbazol-9-yl)desmycosin
20-DH-DO-20-(octahydroazocin-1-yl)tylosin
20-DH-DO-20-(3-azabicyclo[3.2.2]nonan-3-yl)tylosin
20-DH-DO-20-(4-phenyl-1,2,3,6-tetrahydropyridin-1-yl)desmycosin
20-DH-DO-20-(4-benzyl-piperidin-1-yl)desmycosin
20-DH-DO-20-[4-(ethylenedioxy)piperidin-1-yl]desmycosin
20-DH-DO-20-(octahydroazocin-1-yl)macrocin
20-DH-DO-20-(hexahydroazepin-1-yl)actenocin.

EXAMPLES 33–36

20-DH-DO-20-(3,3,5-Trimethylhexahydroazepin-1-yl)desmycosin was prepared by the method of Example 8 and then separated into individual isomers 1 and 2 by silica-gel flash chromatography.

20-DH-DO-20-(Dodecahydrocarbazol-9-yl) desmycosin (compound D25) was a mixture of two isomers. The mixture was separated into two fractions, each of which was rich in one of the isomers, by silica-gel flash chromatography. Each of the isomer-enriched fractions had an activity pattern similar to that of the mixture.

EXAMPLES 37–38

20-DH-DO-20-(Octahydroazocin-1-yl)desmycosin dihydrochloride and tartrate salts were prepared from 20-DH-DO-20-(octahydroazocin-1-yl)desmycosin, using standard procedures.

EXAMPLE 39

A.

Purification of cis-3,5-Dimethylpiperidine

A solution containing 3,5-dimethylpiperidine (40 ml, a 4:1 mixture of cis:trans isomers), triethylamine (42 ml) and dichloromethane (250 ml) was stirred while o-chlorobenzoyl chloride (38.2 ml) was added dropwise at a rate sufficient to maintain gentle reflux. At the completion of the addition, the solution was stirred another half hour; then ten percent aqueous ammonium chloride solution (200 ml) and sufficient conc. HCl to make the aqueous layer acidic were added. The organic layer was separated, washed with brine, dried and concentrated. The solid obtained was recrystallized twice from CH$_2$Cl$_2$ and hexane to give essentially pure cis-amide, mp 99°–103° C.

The amide (17 g) was dissolved in ethylene glycol. Potassium hydroxide pellets (11 g) were added, and the solution was heated to reflux. After one hour, the flask was arranged for downward distillation, and the fraction boiling between 100° C. and 195° C. was collected. This material was partitioned between water and ether, dried and concentrated to afford pure cis-3,5-dimethylpiperidine.

B.

Alternate Purification of cis-3,5-Dimethylpiperidine

A 1-liter, 3-neck flask was charged with 48 ml (0.36 mol) of commercial grade 3,5-dimethylpiperidine (ca. 80–85% cis) and 600 ml of anhydrous ether. HCl gas was bubbled through the solution with vigorous stirring until no free amine remained. The product which formed was separated by filtration and air-dried to give 47 g of the hydrochloride salt, mp 160°–180° C.

The salt was suspended in acetone (600 ml) and heated to reflux for 1 hr. The reaction mixture was cooled to 50° C. and filtered; the separated solid was air-dried to yield 25.6 g of product, mp 226°–228° C. A portion of this material (18 g) was dissolved in water (100 ml), and the solution was adjusted to pH 10 with sodium hydroxide pellets. The free amine was extracted into diethyl ether, dried over magnesium sulfate, filtered and carefully concentrated to yield 8.5 ml of cis-3,5-dimethylpiperidine, contaminated with ≦5% of the trans isomer.

C.

Preparation of cis-20-DH-DO-20-(3,5-dimethylpiperidin-1-yl)desmycosin

Desmycosin (10 g, 12.9 mmol) was dissolved in dry methanol (100 ml), and cis-3,5-dimethylpiperidine (4 g, 35 mmol) was added. After the mixture was stirred for 30 minutes at room temperature, sodium cyanoborohydride (0.8 g, 12.9 mmol) was added. The solution was stirred overnight and then was evaporated under reduced pressure. The residue was partitioned between ethyl acetate and water (150 ml each). The organic layer was then extracted sequentially with pH 6.5 phosphate buffer (100 ml) and pH 4.5 phosphate buffer (100 ml).

The latter solution was then adjusted to pH 10 with 5N sodium hydroxide, and the free amine was reextracted into ethyl acetate. The solution was dried over magnesium sulfate, filtered and concentrated to yield 6.0 g of 20-DH-DO-20-(cis-3,5-dimethylpiperidine-1-yl)desmycosin. Analysis of the product by reverse-phase HPLC detected no trans-isomer.

EXAMPLE 40

Separation of cis- and trans-20-DH-DO-20-(3,5-dimethylpiperidin-1-yl)desmycosin

20-DH-DO-20-(3,5-dimethylpiperidin-1-yl)desmycosin was prepared using 3,5-dimethylpiperidine which was a mixture of cis:trans-isomers (4:1). The product was chromatographed over silica gel using a methanol:dichloromethane:ammonium hydroxide (49.5:49.5:1) solvent system. A single major peak was eluted. The first ten percent of this peak consisted of pure cis-isomer, and the last ten percent consisted of enriched trans-isomer (cis:trans material in a ratio of 16:84.

Tables XIV–XVI summarize certain physical data on exemplified compounds:

TABLE XIV

Physical Characteristics of C-20-Modified Derivatives of Desmycosin

| 20-Substituent | Compound[a] No. | FDMS Parent Ion (m$^+$ + 1) | UV λmax(ε)[b] | Titratable groups[c] | TLC[d] R$_f$ |
|---|---|---|---|---|---|
| pyrrolidin-1-yl | D1 | 827 | | 7.9, 9.5 | 0.30 |
| 4-phenylpiperdin-1-yl | D4 | 917 | 283 (21,800) | | |
| hexahydroazepin-1-yl | D5 | 855 | 282 (21,500) | 7.9, 9.6 | |

TABLE XIV-continued
Physical Characteristics of C-20-Modified Derivatives of Desmycosin

| 20-Substituent | Compound[a] No. | FDMS Parent Ion (m+ + 1) | UV λmax(ε)[b] | Titratable groups[c] | TLC[d] R_f |
|---|---|---|---|---|---|
| hexahydroazepin-1-yl | D5a | 839 | 282 (21,500) | | |
| octahydroazocin-1-yl | D6 | 869 | 282 (21,750) | 7.9, 9.4 | |
| azocyclotridecan-1-yl | D10 | 939 | 282 (19,500) | 8.0, 9.5 | |
| 4-piperidinopiperidin-1-yl | D13 | 924 | 282 (18,600) | 6.0, 9.2 | |
| 3-azabicyclo[3.2.2]nonan-3-yl | D14 | 881 | 282 (20,500) | 7.9, 9.2 | |
| piperidin-1-yl | D2 | 841 | 282 (24,500) | 7.8, 9.1 | |
| 4-hydroxypiperidin-1-yl | D3 | 857 | 282 (20,750) | 7.1, 8.7 | |
| octahydro-1H—azonin-1-yl | D7 | 883 | 282 (20,000) | 7.9, 9.0 | |
| 1,2,3,4-tetrahydroquinolin-1-yl | D11 | 888 | 281 sh (24,500) | | |
| 1,2,3,4-tetrahydroisoquinolin-2-yl | D12 | 888 | 283 (20,600) | | |
| 3-(N,N—diethylcarbamoyl)-piperidin-1-yl] | D15 | 940 | 282 (20,500) | 7.4, 8.6 | |
| 1-azaspiro[4,5]decan-1-yl | D19 | 894 | 282 (21,500) | 7.9, 9.8 | |
| decahydroquinolin-1-yl | D20 | 895 | 282 (21,500) | 7.9, 9.4 | |
| 1,3,3-trimethyl-6-azabicyclo-[3.2.1]octan-1-yl | D21 | 908 | 282 (21,100) | 8.0, 9.7 | |
| 1,2,3,6-tetrahydropyridin-1-yl | D22 | 839 | 282 (21,000) | | |
| 3,3,5-trimethylhexahydroazepin-1-yl, isomer 1 | D23 | 896 | 282 (21,130) | 7.7, 9.0 | |
| 3,3,5-trimethylhexahydroazepin-1-yl, isomer 2 | D24 | 897 | 283 (21,390) | 7.9, 9.4 | |
| dodecahydrocarbazol-9-yl | D25 | 935 | 282(22,500) | 7.95, 9.95 | |
| octahydroazocin-1-yl | D6[e] | | | 7.9, 9.4 | |
| octahydroazocin-1-yl | D6[f] | 869,151 | 282 (19,500) | | 5.4, 7.3, 9.2 |
| cis-3,5-dimethylpiperidin-1-yl | D34 | 869 | 282 (20,000) | | |
| trans-3,5-dimethylpiperidin-1-yl | D35 | 869 | 282 (20,000) | | |
| 3,3-dimethylpiperidin-1-yl | D40 | 869 | 282 (18,900) | | |

[a]Compound numbers from Table II
[b]Run in methanol or ethanol
[c]Run in 66% aqueous DMF
[d]Silicia-gel 60 plates; CH2Cl2MeOH/NH4OH (90:10:0.5) solvent
[e]dihydrochloride salt
[f]tartrate salt

TABLE XV
Physical Characteristics of C-20-Modified Derivatives of Macrocin

| 20-Substituent | Compound[a] No. | FDMS Parent Ion (m+ + 1) | UV λmax(ε)[b] | Titratable groups[c] | TLC[d] R_f |
|---|---|---|---|---|---|
| hexahydroazepin-1-yl | M3 | 985 | | 6.91, 9.40 | 0.26 |
| octahydroazocin-1-yl | M4 | 999 | 282 (24,000) | 6.90, 9.25 | |

[a]Compound numbers from Table III
[b]Run in methanol
[c]Run in 66% aqueous DMF
[d]silica-gel 60 plates: CH2Cl2/MeOH/NH4OH (90:10:0.5) solvent

TABLE XVI
Physical Characteristics of C-20-Modified Derivatives of Lactenocin

| 20-Substituent | Compound[a] No. | FDMS Parent Ion (m+ + 1) | UV λmax (ε) | Titratable groups[d] |
|---|---|---|---|---|
| hexahydroazepin-1-yl | L4 | 841 | 282 (21,500)[b] | 8.0, 9.70 |
| octahydroazocin-1-yl | L5 | 855 | 282 (21,500)[c] | 7.8, 9.3 |

[a]Compound numbers from Table IV
[b]Run in ethanol
[c]Run in methanol
[d]Run in 66% aqueous DMF

EXAMPLES 41-64

The following compounds can be prepared by the methods of the preceeding examples.
20-DH-DO-20-(octahydroazocin-1-yl)tylosin
20-DH-DO-20-(piperidin-1-yl)lactenocin
20-DH-DO-20-(4-hydroxypiperidin-1-yl)DOML
20-DH-DO-20-(decahydroazecin-1-yl)desmycosin
20-DH-DO-20-(octahydroazocin-1-yl)macrocin
20-DH-DO-20-(azacyclotridecan-1-yl)lactenocin
20-DH-DO-20-(hexahydroazepin-1-yl)lactenocin
20-DH-DO-20-(1,2,3,4-tetrahydroisoquinolin-2-yl)macrocin
20-DH-DO-20-(1,2,3,4-tetrahydroquinolin-1-yl)macrocin
20-DH-DO-20-(azacycloundecan-1-yl)desmycosin
20-DH-DO-20-(4-methylpiperidin-1-yl)desmycosin
20-DH-DO-20-(pyrrolidin-1-yl)lactenocin
20-DH-DO-20-(octahydro-1H-azonin-1-yl)tylosin
20-DH-DO-20-(octahydroazocin-1-yl)DOMM
20-DH-DO-20-(octahydroazocin-1-yl)DOML
20-DH-DO-20-(4-phenyl-piperidin-1-yl)lactenocin
20-DH-DO-20-(4-phenylpiperidin-1-yl)-4'-deoxydesmycosin
20-DH-DO-20-(octahydroazocin-1-yl)-4'-deoxydesmycosin 20-DH-DO-20-(3-azabicyclo[3.2.2]nonan-3-yl)-4'-deoxydesmycosin 20-DH-DO-20-(1,2,3,4-tetrahydroisoquinolin-2-yl)lactenocin 20-DH-DO-20-(3,3,5-trimethylhexahydroazepin-1-yl)macrocin 20-DH-DO-20-(decahydrocyclopent[c]azepin-1-yl)desmycosin 20-DH-DO-20-(7-azabicyclo[2.2.1]heptan-7-yl)desmycosin 20-DH-DO-20-(decahydroisoquinolin-2-yl)desmycosin 20-DH-DO-20-(3,5-dimethylpiperidin-1-yl)-4'-deoxydesmycosin 20-DH-DO-20-(3,4-dimethoxypiperidin-1-yl)descomysin 20-DH-DO-20-(3,5-dimethylpiperidin-1-yl)macrocin

EXAMPLE 65

Injectable Formulations (A) A formula 1 base is added to propylene glycol. Water and benzyl alcohol are added so that the solution contains 50% (by volume) propylene glycol, 4% (by volume) benzyl alcohol, and 200 mg/ml of a formula 1 base.

(B) A solution is prepared as described in Section A except that the solution contains 50 mg/ml of a formula 1 base.

(C) A solution is prepared as described in Section A except that the solution contains 350 mg/ml of a formula 1 base.

(D) A solution is prepared as described in Section A except that the solution contains 500 mg/ml of a formula 1 tartrate.

(E) A suspension is prepared by adding a finely ground formula 1 compound to carboxymethyl cellulose with thorough mixing so that the suspension contains 200 mg of the formula 1 base per ml of suspension.

EXAMPLE 66

Chick Ration for Control of Mycoplasma

A balanced, high-energy ration adapted to feed chicks for rapid weight gain is prepared by the following recipe:

| Ingredient | % | lbs |
|---|---|---|
| Ground yellow corn | 50 | 1,000 |
| Soybean meal, solvent-extracted dehulled, finely ground, 50 percent protein | 31.09 | 621.8 |
| Animal fat (beef tallow) | 6.5 | 130 |
| Dried fish meal, with solubles (60% protein) | 5.0 | 100 |
| Distillers' solubles from corn | 4.0 | 80 |
| Dicalcium phosphate, feed grade | 1.8 | 36 |
| Calcium carbonate | 0.8 | 16 |
| Vitamin premix (representing vitamins A, D, E, K and $B_{12}$, choline, niacin, pantothenic acid, riboflavin, biotin, with glucose bulking agent) | 0.5 | 10 |
| Trace mineral premix (representing $MnSO_4$, ZnO, KI, $FeSO_4$, $CaCO_3$) | 0.2 | 4 |
| 2-Amino-4-hydroxybutyric acid (hydroxy analog of methionine) | 0.1 | 2 |
| Formula 1 or 2 compound | 0.01 | 0.2 |

These substances are mixed in accordance with standard feed-mixing techniques. Chicks fed such a ration, with water ad libitum, are protected against exposure to Mycoplasma infections.

We claim:

1. A compound of the formula 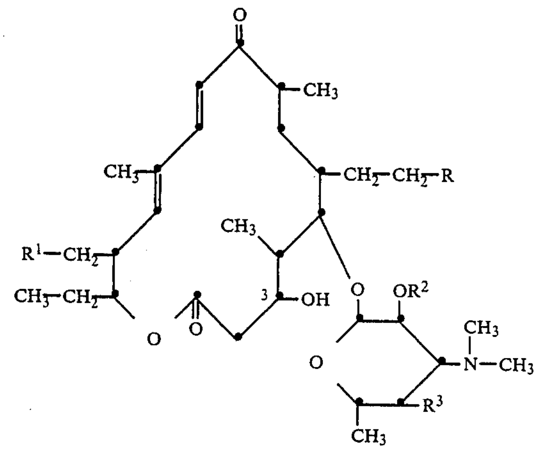 wherein

R is a saturated or unsaturated secondary amino group of the formula in which the nitrogen atom is part of an otherwise carbocyclic ring system selected from a monocyclic ring containing from 5 to 16 ring atoms or a bicyclic or tricyclic ring system containing from 8 to 20 ring atoms or such a group wherein one or more of the carbon atoms is substituted by $C_1$-$C_4$ alkyl, $C_2$-$C_4$ alkenyl, $C_2$-$C_4$ alkynyl, $C_1$-$C_4$ alkoxy, $C_1$-$C_4$ alkoxycarbonyl, hydroxyl, $C_1$-$C_4$ alkanoyloxy, halo, halo-$C_1$-$C_4$ alkyl, $-N(C_1$-$C_4$ alkyl$)_2$, $-N(CH_2)_m$, cyano, ethylenedioxy, benzyl, phenyl, or phenyl substituted by from 1 to 3 substituents selected from nitro, halo, $C_1$-$C_4$-alkyl, $C_1$-$C_4$ alkoxy, hydroxy, amino, or mono- or di-($C_1$-$C_4$ alkyl)amino;

m is an integer from 4 through 7;

$R^1$ is

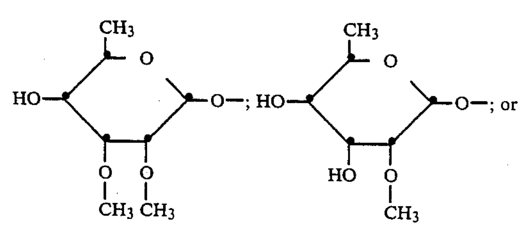

; or

-continued

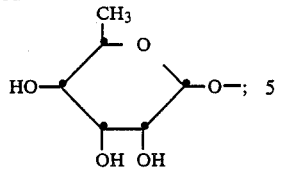

R² is hydrogen; C₁-C₅-alkanoyl or C₁-C₅-alkanoyl having from one to three halo substituents; benzoyl, phenylacetyl or phenylpropionyl or benzoyl, phenylacetyl or phenylpropionyl having from one to five halo or methyl or from one to two methoxyl, nitro or hydroxyl substituents;

R³ is hydroxy; C₁-C₅ alkanoyloxy; C₁-C₅-alkanoyloxy having from one to three halo substituents; benzoyloxy, phenylacetoxy or phenoxyacetoxy or benzoyloxy, phenylacetoxy or phenoxyacetoxy having from one to five halo or methyl of from one to two methoxyl, nitro or hydroxyl substituents; or

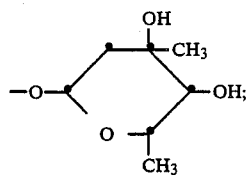

and the acid addition salts thereof.

2. A compound of claim 1 wherein R is a monocyclic ring.

3. A compound of claim 1 wherein R is a bicyclic or tricyclic ring system.

4. A compound of claim 1 wherein R is unsaturated.

5. A compound of claim 1 wherein R is saturated.

6. A compound of claim 1 wherein R¹ is

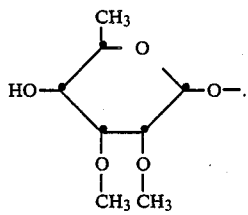

7. A compound of claim 6 wherein R³ is hydroxy.

8. A compound of claim 2 wherein R is octahydroazocin-1-yl, hexahydroazepin-1-yl, octahydro-1H-azonin-1-yl, piperidin-1-yl, or 1,2,3,6-tetrahydropyridin-1-yl.

9. The compound of claim 8 which is 20-dihydro-20-deoxy-20-(3,3,5-trimethylhexahydroazepin-1-yl(desmycosin.

10. The compound of claim 8 which is 20-dihydro-20-deoxy-20-(3,5-dimethylpiperidin-1-yl)desmycosin.

11. The compound of claim 10 in the cis configuration.

12. The compound of claim 10 which is in the trans configuration.

13. The compound of claim 8 which is 20-dihydro-20-deoxy-20-deoxy-20-(3,3-dimethylpiperidin-1-yl)desmycosin.

14. A compound of claim 3 wherein R is 1,2,3,4-tetrahydroisoquinolin-1-yl; 1-azaspiro[4.5]decan-1-yl; 3-azaspiro[5.5]undecan-3-yl; azabicyclononanyl; decahydroquinolin-1-yl; 1,8,8-trimethyl-3-azabicyclo[3.2.1]octan-3-yl; 1,3,3-trimethyl-6-azabicyclo[3.2.1]octan-6-yl, or dodecahydrocarbazol-9-yl.

15. The compound of claim 14 which is 20-dihydro-20-deoxy-20-[3-azabicyclo[3.2.2]nonan-3-yl]desmycosin.

16. A compound of claim 3 wherein R is 2,3-dihydroindol-1-yl, octahydroisoindol-2-yl, or octahydroindol-1-yl.

17. A compound of the formula

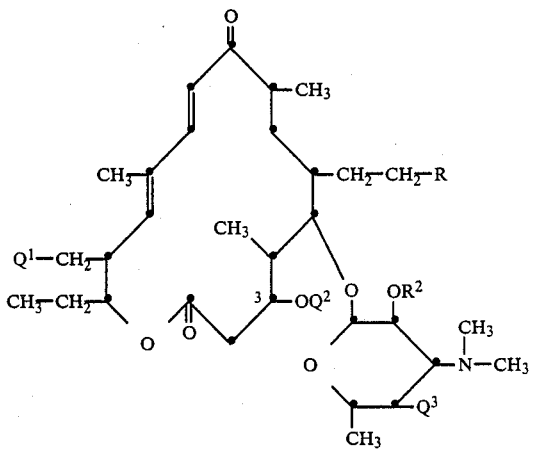

wherein
Q¹ is

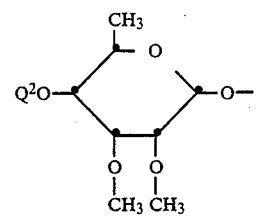

Q² is hydrogen or a hydroxyl-protecting group;
Q³ is hydrogen or iodo;
R is a saturated or unsaturated secondary amino group of the formula

in which the nitrogen atom is part of an otherwise carbocyclic ring system selected from a monocyclic ring containing from 5 to 16 ring atoms or a bicyclic or tricyclic ring system containing from 8 to 20 ring atoms or such a group wherein one or more of the carbon atoms is substituted by C₁-C₄ alkyl, C₂-C₄ alkenyl, C₂-C₄ alkynyl, C₁-C₄ alkoxy, C₁-C₄ alkoxycarbonyl, hydroxyl, C₁-C₄ alkanoyloxy, halo, halo-C₁-C₄ alkyl, —N(C₁-C₄ alkyl)₂, —N(CH₂)ₘ,

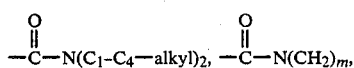

cyano, ethylenedioxy, benzyl, phenyl, or phenyl substituted by from 1 to 3 substituents selected from nitro, halo, $C_1$–$C_4$-alkyl, $C_1$–$C_4$ alkoxy, hydroxy, amino, or mono- or di-($C_1$–$C_4$ alkyl)amino;

m is an integer from 4 through 7;

$R^2$ is hydrogen; $C_1$–$C_5$-alkanoyl or $C_1$–$C_5$-alkanoyl having from one to three halo substituents; benzoyl, phenylacetyl or phenylpropionyl or benzoyl, phenylacetyl or phenylpropionyl having from one to five halo or methyl or from one to two methoxyl, nitro or hydroxyl substituents;

and the acid addition salts thereof.

18. A compound of claim 17 wherein R is a monocyclic ring.

19. A compound of claim 17 wherein R is a bicyclic or tricyclic ring system.

20. A compound of claim 17 wherein R is unsaturated.

21. A compound of claim 17 wherein R is saturated.

22. A compound of claim 17 wherein $Q^2$ and $Q^3$ are hydrogen.

23. A compound of claim 18 wherein R is octahydroazocin-1-yl, hexahydroazepin-1-yl, octahydro-1H-azonin-1-yl, piperidin-1-yl or 1,2,3,6-tetrahydropyridin-1-yl.

24. The compound of claim 23 which is 20-dihydro-20-deoxy-20-(3,5-dimethylpiperidin-1-yl)-4'-deoxydesmycosin.

25. A compound of claim 19 wherein R is 1,2,3,4-tetrahydroisoquinolin-1-yl; 1-azaspiro[4.5]decan-1-yl; 3-azaspiro[5.5]undecan-1-yl; 3-azabicyclo[3.2.2]nonan-3-yl; decahydroquinolin-1-yl; 1,8,8-trimethyl-3-azabicyclo[3.2.1]octan-3-yl; 6-azabicyclo[3.2.1]octan-6-yl; or dodecahydrocarbazol-9-yl.

26. A compound of claim 1 wherein
R is selected from
(a) a saturated monocyclic amino group;
(b) a saturated monocyclic amino group which is substituted at one or more of the carbon atoms by a $C_1$–$C_3$-alkyl, hydroxyl, —$N(R^4)_2$,

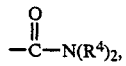

carbomethoxy, carboethoxy, or phenyl group; or
(c) a bicyclic or tricyclic ring system selected from 1,2,3,4-tetrahydro-quinolin-1-yl; decahydroquinolin-1-yl; 1,2,3,4-tetrahydroisoquinolin-2-yl; decahydroisoquinolin-2-yl; indolin-1-yl; isoindolin-2-yl; decahydrocyclohepta[b]pyrrol-1-yl; decahydrocyclohepta[c]pyrrol-2-yl; decahydrocyclopent[c]azepin-2-yl; decahydrocyclopent[d]azepin-3-yl; 2,3,4,5-tetrahydro-1H-2-benzazepin-2-yl; 2,3,4,5-tetrahydro-1H-3-benzazepin-3-yl; azabicycloheptanyl; azabicyclooctanyl; azabicyclononanyl; azabicyclodecanyl or azatricyclodecanyl; and
$R^4$ is methyl, ethyl, n-propyl or isopropyl or the $R^4$ groups taken together form a polymethylene moiety such that —$N(R^4)_2$ constitutes a cyclic amino group selected from pyrrolidinyl, piperidinyl, hexahydroazepinyl or octahydroazocinyl;

and the acid addition salts thereof.

27. A compound of claim 26 wherein R is octahydroazocin-1-yl or substituted octahydroazocin-1-yl.

28. A compound of claim 27 wherein R is octahydroazocin-1-yl.

29. A compound of claim 26 wherein R is hexahydroazepin-1-yl or substituted hexahydroazepin-1-yl.

30. A compound of claim 29 wherein R is hexahydroazepin-1-yl.

31. A compound of claim 26 wherein R is piperidin-1-yl or substituted piperidin-1-yl.

32. The compound of claim 31 which is 20-dihydro-20-deoxy-20-(4-hydroxypiperidin-1-yl)desmycosin.

33. The compound of claim 31 which is 20-dihydro-20-deoxy-20-(4-piperidinopiperidin-1-yl)desmycosin.

34. A compound of claim 31 wherein R is piperidin-1-yl.

35. A compound of claim 26 wherein $R^2$ is $C_1$–$C_5$-alkanoyl or substituted $C_1$–$C_5$-alkanoyl.

36. A compound of claim 35 wherein $R^2$ is acetyl or propionyl.

37. A compound of claim 17 wherein
R is selected from
(a) a saturated monocyclic amino group;
(b) a saturated monocyclic amino group which is substituted at one or more of the carbon atoms by a $C_1$–$C_3$-alkyl, hydroxyl, —$N(R^4)_2$,

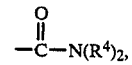

carbomethoxy, carboethoxy, or phenyl group; or
(c) a bicyclic or tricyclic ring system selected from 1,2,3,4-tetrahydro-quinolin-1-yl; decahydroquinolin-1-yl; 1,2,3,4-tetrahydroisoquinolin-2-yl; decahydroisoquinolin-2-yl; indolin-1-yl; isoindolin-2-yl; decahydrocyclohepta[b]pyrrol-1-yl; decahydrocyclohepta[c]pyrrol-2-yl; decahydrocyclopent[c]azepin-2-yl; decahydrocyclopent[d]azepin-3-yl; 2,3,4,5-tetrahydro-1H-2-benzazepin-2-yl; 2,3,4,5-tetrahydro-1H-3-benzazepin-3-yl; azabicycloheptanyl; azabicyclooctanyl; azabicyclononanyl; azabicyclodecanyl or azatricyclodecanyl; and
$R^4$ is methyl, ethyl, n-propyl or isopropyl or the $R^4$ groups taken together form a polymethylene moiety such that —$N(R^4)_2$ constitutes a cyclic amino group selected from pyrrolidinyl, piperidinyl, hexahydroazepinyl or octahydroazocinyl;

and the acid addition salts thereof.

38. A compound of claim 37 wherein R is octahydroazocin-1-yl or substituted octahydroazocin-1-yl.

39. A compound of claim 37 wherein R is hexahydroazepin-1-yl or substituted hexahydroazepin-1-yl.

40. A compound of claim 37 wherein $R^2$ is $C_1$–$C_5$-alkanoyl or substituted $C_1$–$C_5$-alkanoyl.

41. A compound of claim 40 wherein $R^2$ is acetyl or propionyl.

42. The compound of claim 28 which is 20-dihydro-20-deoxy-20-(octahydroazocin-1-yl)desmycosin.

43. The compound of claim 30 which is 20-dihydro-20-deoxy-20-(hexahydroazepin-1-yl)desmycosin.

44. The compound of claim 34 which is 20-dihydro-20-deoxy-20-(piperidin-1-yl)desmycosin.

45. The compound of claim 31 which is 20-dihydro-20-deoxy-20-(4-phenylpiperidin-1-yl)desmycosin.

46. The compound of claim 38 which is 20-dihydro-20-deoxy-20-(octahydroazocin-1-yl)-4'-deoxydesmycosin.

47. The compound of claim 39 which is 20-dihydro-20-deoxy-20-(hexahydroazepin-1-yl)-4'-deoxydesmycosin.

48. A composition useful for the treatment of bacterial or mycoplasmal infections comprising an effective amount of a compound of claim 1 or a pharmaceutically acceptable acid addition salt thereof and a suitable pharmaceutical vehicle.

49. A composition useful for the treatment of bacterial or mycoplasmal infections comprising an effective amount of a compound of claim 17 or a pharmaceutically acceptable acid addition salt thereof and a suitable pharmaceutical vehicle.

50. A method for treating infections caused by Mycoplasma species which comprises administering parenterally to an infected or susceptible warm-blooded animal an effective amount of a composition of claim 48 which is effective against the Mycoplasma species.

51. A method for treating infections caused by Mycoplasma species which comprises administering parenterally to an infected or susceptible warm-blooded animal an effective amount of a composition of claim 49 which is effective against the Mycoplasma species.

52. A method for treating infections caused by susceptible gram-positive bacteria which comprises administering to an infected or suceptible warm-blooded animal an effective amount of a composition of claim 48 which is effective against said infection.

53. A method for treating infections caused by susceptible gram-positive bacteria which comprises administering to an infected or susceptible warm-blooded animal an effective amount of a composition of claim 49 which is effective against said infection.

54. A method for treating infections caused by Pasteurella species which comprises administering to an infected or susceptible warm-blooded animal an effective amount of a composition of claim 48 which is effective against said infection.

55. A method for treating infections caused by Pasteurella species which comprises administering to an infected or susceptible warm-blooded animal an effective amount of of a composition of claim 49 which is effective against said infection.

56. A composition useful for the treatment of bacterial or mycoplasmal infections comprising an effective amount of a compound of claim 26 or a pharmaceutically acceptable acid addition salt thereof and a suitable pharmaceutical vehicle.

57. A composition useful for the treatment of bacterial or mycoplasmal infections comprising an effective amount of a compound of claim 37 or a pharmaceutically acceptable acid addition salt thereof and a suitable pharmaceutical vehicle.

58. A method for treating infections caused by Mycoplasma species which comprises administering parenterally to an infected or susceptible warm-blooded animal an amount of a composition of claim 56 which is effective against the Mycoplasma species.

59. A method for treating infections caused by Mycoplasma species which comprises administering parenterally to an infected or susceptible warm-blooded animal an amount of a composition of claim 57 which is effective against the Mycoplasma species.

60. A method for treating infections caused by gram-positive bacteria which comprises administering to an infected or susceptible warm-blooded animal an amount of a composition of claim 56 which is effective against said infection.

61. A method for treating infections caused by gram-positive bacteria which comprises administering to an infected or susceptible warm-blooded animal an amount of a composition of claim 57 which is effective against said infection.

62. A method for treating infections caused by Pasteuralla species which comprises administering to an infected or susceptible warm-blooded animal an amount of a composition of claim 56 which is effective against said infection.

63. A method for treating infections caused by Pasteurella species which comprises administering to an infected or susceptible warm-blooded animal an amount of a composition of claim 57 which is effective against said infection.

* * * * *